US007541170B2

(12) United States Patent
Wang et al.

(10) Patent No.: US 7,541,170 B2
(45) **Date of Patent: *Jun. 2, 2009**

(54) NUCLEIC ACID MODIFYING ENZYMES

(75) Inventors: Yan Wang, San Francisco, CA (US); Lei Xi, Foster City, CA (US); Dennis E. Prosen, Foster City, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/870,353

(22) Filed: May 30, 2001

(65) Prior Publication Data

US 2003/0162173 A1 Aug. 28, 2003

Related U.S. Application Data

(63) Continuation-in-part of application No. 09/640,958, filed on Aug. 16, 2000, now Pat. No. 6,627,424.

(60) Provisional application No. 60/207,567, filed on May 26, 2000.

(51) Int. Cl.
*C12N 9/12* (2006.01)
*C07K 1/00* (2006.01)

(52) U.S. Cl. ...................... 435/194; 435/183; 435/69.1; 435/455; 530/350; 530/358; 536/23.1; 536/23.2; 536/23.4; 536/23.7

(58) Field of Classification Search ................. 435/194, 435/183, 69.1, 455; 530/350, 358; 536/23.1, 536/23.2, 23.3, 23.4, 23.7
See application file for complete search history.

(56) References Cited

U.S. PATENT DOCUMENTS 5,474,911 A 12/1995 Pontius et al. ................ 435/41
5,972,603 A 10/1999 Bedford et al. ................ 435/6
6,228,628 B1 5/2001 Gelfand et al. .............. 435/194
6,627,424 B1 * 9/2003 Wang ......................... 435/194

FOREIGN PATENT DOCUMENTS

DE 198 40 771 A1 2/2000

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

Shehi et al. "Thermal Stability and DNA Binding Activity of a Variant Form of Sso7d Protein from the Archeon *Sulfolobus solfataricus* Truncated at Leucine 54", Biochemistry, 2003 v. 42 pp. 8362-8368.*

Consonni et al. "A single point mutation in the Extreme Heat- and Pressure-Resistant Sso7d Protein from *Sulfolobus solfataricus* Leads to a Major Rearrangement of the Hydrophobis Core", Biochemistry, 1999, vol. 38, pp. 12709-12717.*

Wang et al. "A Novel Strategy to Enginner DNA Polymerases for Enhanced Processivity and Improved Performance in vitro", Nucleic Acid Research, vol. 32, pp. 1197-1207.*

Carrodeguas et al., "The Accessory Subunit of *Xenopus laevis* Mitochondrial DNA Polymerase γ Increases Processivity of the Catalytic Subunit of Human DNA Polymerase γ and is Related to Class II Aminoacyl-tRNA Synthetases," *Molecular and Cellular Biology* (Jun. 1999) 19(6): 4039-4046.

Baumann et al., "Solution Structure and DNA-binding Properties of a Thermostable Protein from the Archaeon *Sulfolobus solfataricus*" *Structural Biology* (1994) vol. 1(11), pp. 808-819.

Bedford, et al. "The Thioredoxin Binding Domain of Bacteriophage T7 DNA Polymerase Confers Processivity on *Escherichia coli* DNA Polymerase I" *Proc. Natl. Acad. Sci. USA* (Jan. 1997) vol. 94, pp. 479-484.

Cann et al., "Functional Interactions of a Homolog of Proliferating Cell Nuclear Antigen with DNA Polymerases in *Archaea," Journal of Bacteriology* (1999) vol. 181(21), pp. 6591-6599.

Choli et al., "Isolation, Characterization and Microsequence Analysis of a Small Basic Methylated DNA-binding Protein from the Archaebacterium, *Sulfolobus solfataricus" Biochimica et Biophbysica Acta* (1988) vol. 950, pp. 193-203.

De Felice et al., "Two DNA polymerase Sliding Clamps from the Thermophilic Archaeon *Sulfolobus solfataricus" J. Molec. Biol.* (1999) vol. 291, pp. 47-57.

Gao et al., "The Crystal Structure of the Hyperthermophile Chromosomal Protein Sso7d Bound to DNA" *Nature Structural Biology* (1998) vol. 5(9), pp. 782-786.

Lim, et al. "The Mitochondrial p55 Accessory Subunit of Human DNA Polymerase γ Enhances DNA Binding, Promotes Processive DNA Synthesis, and Confers N-Ethylmaleimide Resistance" *J. Biological Chemistry* (Dec. 1999) vol. 274(53), pp. 38197-38203.

McAfee, et al., "Gene Cloning, Expression, and Characterization of the Sac7 Proteins From the Hyperthermophile *Sulfolobus acidocaldarius" Biochemistry* (1995) vol. 34, pp. 10063-10077.

Sandman, et al., "Histone-encoding Genes from *Pyrococcus*: Evidence for Members of the HMf Family of Archaeal Histones in a Non-methanogenic Archeaon" Gene (1994) vol. 150, pp. 207-208.

Shamoo, et al. "Building a Replisome from Interacting Pieces: Sliding Clamp Complexed to a Peptide from DNA Polymerase and a Polymerase Editing Complex" *Cell* (1999) vol. 99 pp. 155-166.

Starich, et al., "NMR Structure of HMfB from the Hyperthermophile, *Methanothermus fervidus,* Confirms that this Archaeal Protein is a Histone" *J. Molec. Biol.* (1996) vol. 255 pp. 187-203.

Zhang et al., "Expression and Psysicochemical Characterization of Human Proliferating Cell Nuclear Antigen" *Biochemistry* (1995) vol. 34, pp. 10703-10712.

Robinson, Howard et al.; "The hyperthermophile chromosomal protein Sac7d sharply kinks DNA"; *Nature*; Mar. 12, 1998; pp. 202-205; vol. 392; Macmillan Publishers Ltd.

Wang, Yan et al.; "A novel strategy to engineer DNA polymerases for enhanced processivity and improved performance in vitro"; *Nucleic Acids Research*; 2004; pp. 1197-1207; vol. 32, No. 3; Oxford University Press.

Weisshart, Klaus, et al., "Herpes Simplex Virus Processivity Factor UL42 Imparts Increased DNA-Binding Specificity to the Viral DNA Polymerase and Decreased Dissociation from Primer-Template without Reducint the Elongation Rate," *Journal of Virolosy* (Jan. 1999) 73(1): 55-66.

* cited by examiner

*Primary Examiner*—Richard G Hutson
(74) *Attorney, Agent, or Firm*—Townsend and Townsend and Crew LLP

(57) ABSTRACT

This invention provides for an improved generation of novel nucleic acid modifying enzymes. The improvement is the fusion of a sequence-non-specific nucleic-acid-binding domain to the enzyme in a manner that enhances the ability of the enzyme to bind and catalytically modify the nucleic acid.

23 Claims, 3 Drawing Sheets

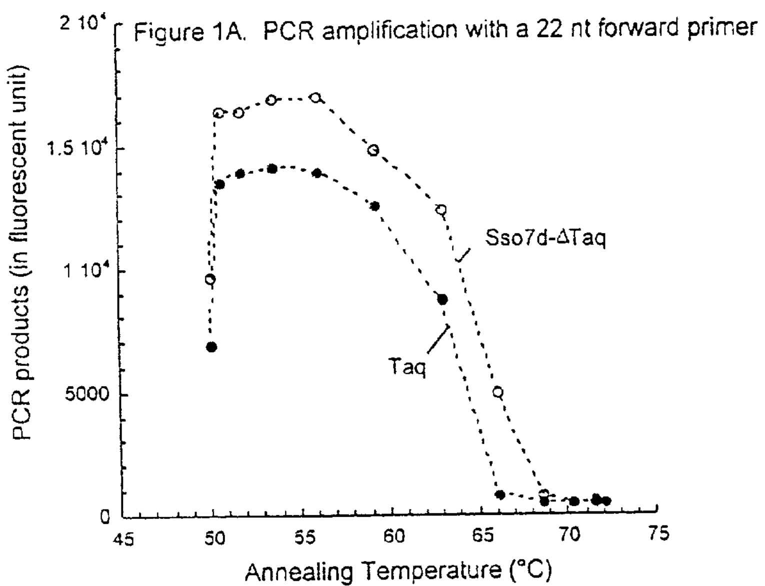
Figure 1A. PCR amplification with a 22 nt forward primer
PCR products (in fluorescent unit)
Annealing Temperature (°C)
Sso7d-ΔTaq
Taq
2 10⁴
1.5 10⁴
1 10⁴
5000
0
45
50
55
60
65
70
75

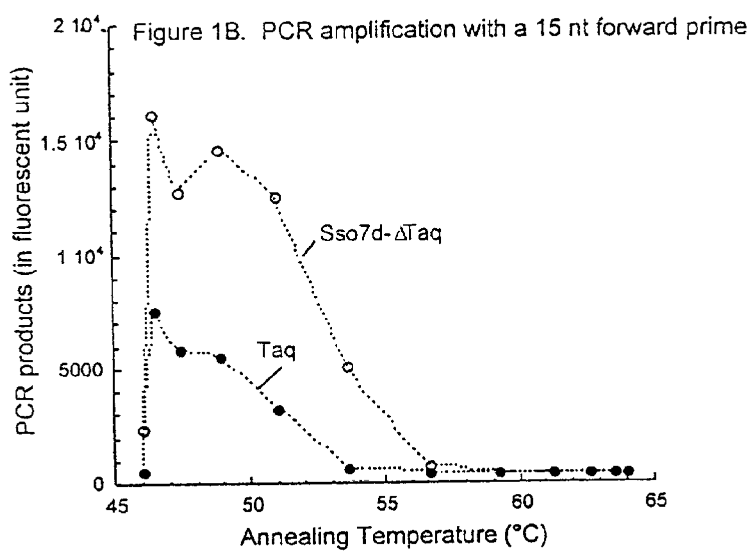
Figure 1B. PCR amplification with a 15 nt forward prime
PCR products (in fluorescent unit)
Annealing Temperature (°C)
Sso7d-ΔTaq
Taq
2 10⁴
1.5 10⁴
1 10⁴
5000
0
45
50
55
60
65

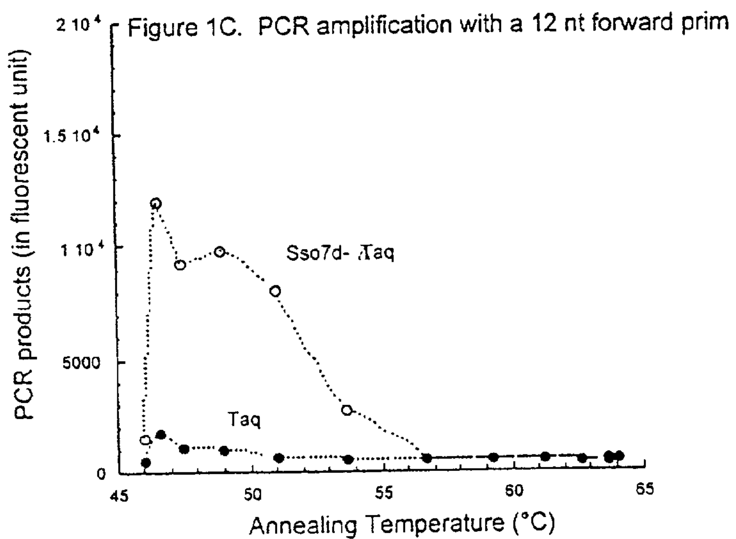
Figure 1C. PCR amplification with a 12 nt forward prim
PCR products (in fluorescent unit)
Annealing Temperature (°C)
Taq
2 10⁴
1.5 10⁴
1 10⁴
5000
0
45
50
55
60
65

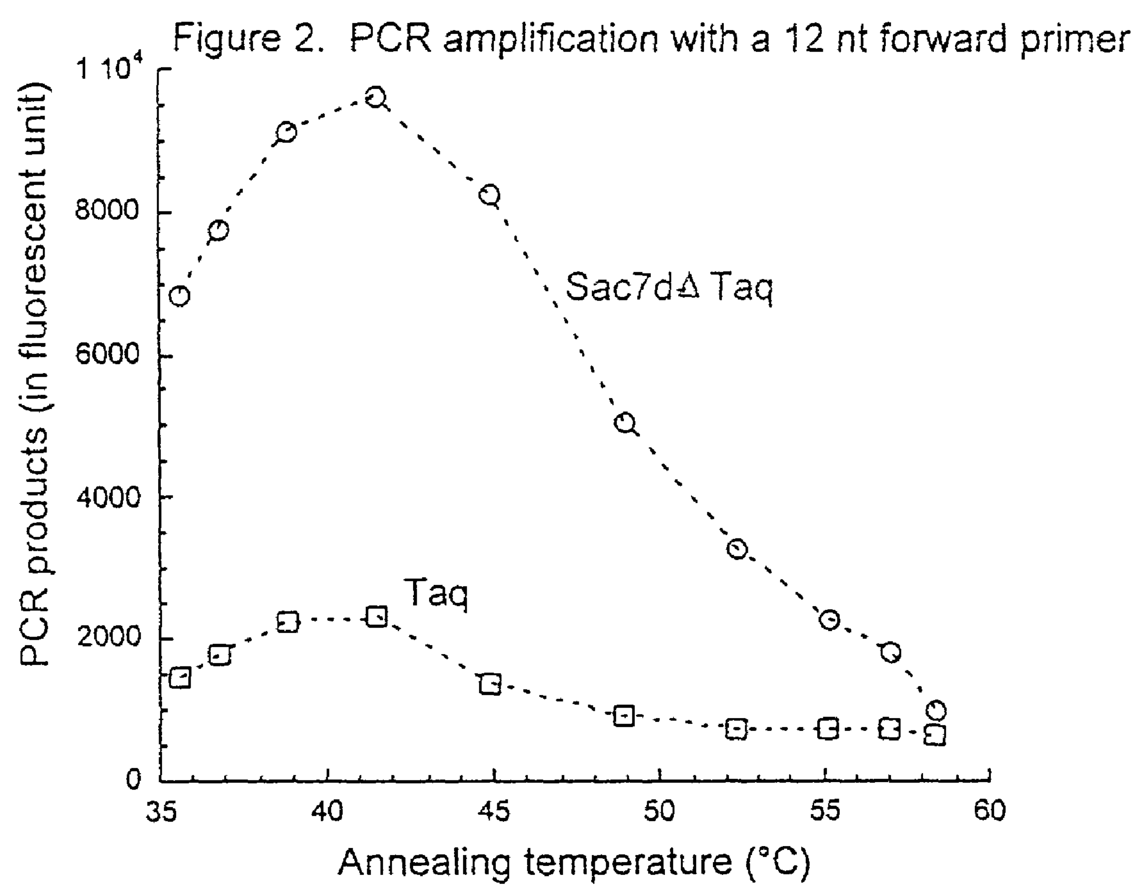
Figure 2. PCR amplification with a 12 nt forward primer
PCR products (in fluorescent unit)
1 10^4
8000
6000
4000
2000
0
35
40
45
50
55
60
Annealing temperature (°C)
Sac7dΔ Taq
Taq

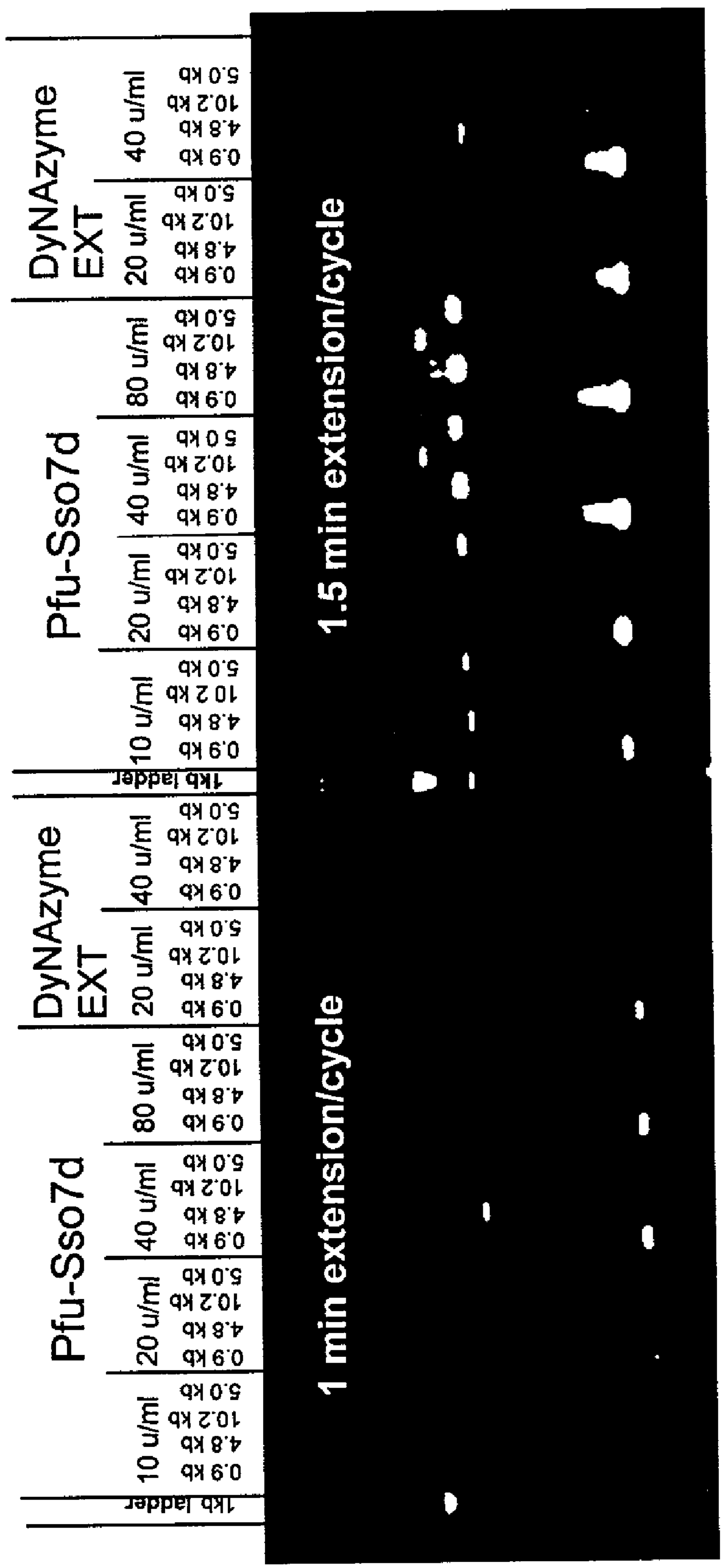
Figure 3. Pfu-Sso7d is more efficient than DyNAzyme EXT in long PCR.

SEQUENCE LISTING

```
<160> NUMBER OF SEQ ID NOS: 34

<210> SEQ ID NO 1
<211> LENGTH: 189
<212> TYPE: DNA
<213> ORGANISM: Artificial Sequence
<220> FEATURE:
<223> OTHER INFORMATION: Description of Artificial Sequence:synthetic
      sequence non-specific double-stranded nucleic acid
      binding protein Ssod7d
<220> FEATURE:
<221> NAME/KEY: CDS
<222> LOCATION: (1)..(189)
<223> OTHER INFORMATION: Ssod7d

<400> SEQUENCE: 1

gcaaccgtaa agttcaagta caaaggcgaa gaaaaagagg tagacatctc caagatcaag      60

aaagtatggc gtgtgggcaa gatgatctcc ttcacctacg acgagggcgg tggcaagacc     120

ggccgtggtg cggtaagcga aaaggacgcg ccgaaggagc tgctgcagat gctggagaag     180

cagaaaaag                                                             189


<210> SEQ ID NO 2
<211> LENGTH: 63
<212> TYPE: PRT
<213> ORGANISM: Artificial Sequence
<220> FEATURE:
<223> OTHER INFORMATION: Description of Artificial Sequence:synthetic
      sequence non-specific double-stranded nucleic acid
      binding protein Ssod7d

<400> SEQUENCE: 2

Ala Thr Val Lys Phe Lys Tyr Lys Gly Glu Glu Lys Glu Val Asp Ile
  1               5                  10                  15

Ser Lys Ile Lys Lys Val Trp Arg Val Gly Lys Met Ile Ser Phe Thr
             20                  25                  30

Tyr Asp Glu Gly Gly Gly Lys Thr Gly Arg Gly Ala Val Ser Glu Lys
         35                  40                  45

Asp Ala Pro Lys Glu Leu Leu Gln Met Leu Glu Lys Gln Lys Lys
     50                  55                  60


<210> SEQ ID NO 3
<211> LENGTH: 1899
<212> TYPE: DNA
<213> ORGANISM: Artificial Sequence
<220> FEATURE:
<223> OTHER INFORMATION: Description of Artificial Sequence:fusion
      protein Ssod7d-deltaTaq
<220> FEATURE:
<221> NAME/KEY: CDS
<222> LOCATION: (1)..(1899)
<223> OTHER INFORMATION: Ssod7d-deltaTaq
```

-continued

<400> SEQUENCE: 3

```
atgattacga attcgagcgc aaccgtaaag ttcaagtaca aaggcgaaga aaaagaggta     60

gacatctcca agatcaagaa agtatggcgt gtgggcaaga tgatctcctt cacctacgac    120

gagggcggtg gcaagaccgg ccgtggtgcg gtaagcgaaa aggacgcgcc gaaggagctg    180

ctgcagatgc tggagaagca gaaaaagggc ggcggtgtca ctagtcccaa ggccctggag    240

gaggccccct ggcccccgcc ggaaggggcc ttcgtgggct ttgtgctttc ccgcaaggag    300

cccatgtggg ccgatcttct ggccctggcc gccgccaggg ggggccgggt ccaccgggcc    360

cccgagcctt ataaagccct cagggacctg aaggaggcgc gggggcttct cgccaaagac    420

ctgagcgttc tggccctgag ggaaggcctt ggcctcccgc ccggcgacga ccccatgctc    480

ctcgcctacc tcctggaccc ttccaacacc acccccgagg gggtggcccg gcgctacggc    540

ggggagtgga cggaggaggc gggggagcgg gccgcccttt ccgagaggct cttcgccaac    600

ctgtggggga ggcttgaggg ggaggagagg ctcctttggc tttaccggga ggtggagagg    660

ccccttttccg ctgtcctggc ccacatggag gccacggggg tgcgcctgga cgtggcctat    720

ctcagggcct tgtccctgga ggtggccgag gagatcgccc gcctcgaggc cgaggtcttc    780

cgcctggccg gccacccctt caacctcaac tcccgggacc agctggaaag ggtcctcttt    840

gacgagctag ggcttcccgc catcggcaag acggagaaga ccggcaagcg ctccaccagc    900

gccgccgtcc tggaggccct ccgcgaggcc caccccatcg tggagaagat cctgcagtac    960

cgggagctca ccaagctgaa gagcacctac attgacccct tgccggacct catccacccc   1020

aggacgggcc gcctccacac ccgcttcaac cagacggcca cggccacggg caggctaagt   1080

agctccgatc ccaacctcca gaacatcccc gtccgcaccc cgcttgggca gaggatccgc   1140

cgggccttca tcgccgagga ggggtggcta ttggtggccc tggactatag ccagatagag   1200

ctcagggtgc tggcccacct ctccggcgac gagaacctga tccgggtctt ccaggagggg   1260

cgggacatcc acacggagac cgccagctgg atgttcggcg tcccccggga ggccgtggac   1320

cccctgatgc gccgggcggc caagaccatc aacttcgggg tcctctacgg catgtcggcc   1380

caccgcctct cccaggagct agccatccct tacgaggagg cccaggcctt cattgagcgc   1440

tactttcaga gcttccccaa ggtgcgggcc tggattgaga agaccctgga ggagggcagg   1500

aggcgggggt acgtggagac cctcttcggc cgccgccgct acgtgccaga cctagaggcc   1560

cgggtgaaga gcgtgcggga ggcggccgag cgcatggcct tcaacatgcc cgtccagggc   1620

accgccgccg acctcatgaa gctggctatg gtgaagctct tccccaggct ggaggaaatg   1680

gggggccagga tgctccttca ggtccacgac gagctggtcc tcgaggcccc aaaagagagg   1740

gcggaggccg tggcccggct ggccaaggag gtcatggagg gggtgtatcc cctggccgtg   1800

cccctggagg tggaggtggg gataggggag gactggctct ccgccaagga gggcattgat   1860

ggccgcggcg gaggcgggca tcatcatcat catcattaa                          1899
```

<210> SEQ ID NO 4
<211> LENGTH: 632
<212> TYPE: PRT
<213> ORGANISM: Artificial Sequence
<220> FEATURE:
<223> OTHER INFORMATION: Description of Artificial Sequence:fusion
      protein Ssod7d-deltaTaq -continued

<400> SEQUENCE: 4

```
Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Trp Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Gly Val Thr Ser Pro Lys Ala Leu Glu
 65                  70                  75                  80

Glu Ala Pro Trp Pro Pro Pro Glu Gly Ala Phe Val Gly Phe Val Leu
                 85                  90                  95

Ser Arg Lys Glu Pro Met Trp Ala Asp Leu Leu Ala Leu Ala Ala Ala
            100                 105                 110

Arg Gly Gly Arg Val His Arg Ala Pro Glu Pro Tyr Lys Ala Leu Arg
        115                 120                 125

Asp Leu Lys Glu Ala Arg Gly Leu Leu Ala Lys Asp Leu Ser Val Leu
    130                 135                 140

Ala Leu Arg Glu Gly Leu Gly Leu Pro Pro Gly Asp Asp Pro Met Leu
145                 150                 155                 160

Leu Ala Tyr Leu Leu Asp Pro Ser Asn Thr Thr Pro Glu Gly Val Ala
                165                 170                 175

Arg Arg Tyr Gly Gly Glu Trp Thr Glu Glu Ala Gly Glu Arg Ala Ala
            180                 185                 190

Leu Ser Glu Arg Leu Phe Ala Asn Leu Trp Gly Arg Leu Glu Gly Glu
        195                 200                 205

Glu Arg Leu Leu Trp Leu Tyr Arg Glu Val Glu Arg Pro Leu Ser Ala
    210                 215                 220

Val Leu Ala His Met Glu Ala Thr Gly Val Arg Leu Asp Val Ala Tyr
225                 230                 235                 240

Leu Arg Ala Leu Ser Leu Glu Val Ala Glu Glu Ile Ala Arg Leu Glu
                245                 250                 255

Ala Glu Val Phe Arg Leu Ala Gly His Pro Phe Asn Leu Asn Ser Arg
            260                 265                 270

Asp Gln Leu Glu Arg Val Leu Phe Asp Glu Leu Gly Leu Pro Ala Ile
        275                 280                 285

Gly Lys Thr Glu Lys Thr Gly Lys Arg Ser Thr Ser Ala Ala Val Leu
    290                 295                 300

Glu Ala Leu Arg Glu Ala His Pro Ile Val Glu Lys Ile Leu Gln Tyr
305                 310                 315                 320

Arg Glu Leu Thr Lys Leu Lys Ser Thr Tyr Ile Asp Pro Leu Pro Asp
                325                 330                 335

Leu Ile His Pro Arg Thr Gly Arg Leu His Thr Arg Phe Asn Gln Thr
            340                 345                 350

Ala Thr Ala Thr Gly Arg Leu Ser Ser Ser Asp Pro Asn Leu Gln Asn
        355                 360                 365

Ile Pro Val Arg Thr Pro Leu Gly Gln Arg Ile Arg Arg Ala Phe Ile
    370                 375                 380

Ala Glu Glu Gly Trp Leu Leu Val Ala Leu Asp Tyr Ser Gln Ile Glu
385                 390                 395                 400

Leu Arg Val Leu Ala His Leu Ser Gly Asp Glu Asn Leu Ile Arg Val
                405                 410                 415
```

```
Phe Gln Glu Gly Arg Asp Ile His Thr Glu Thr Ala Ser Trp Met Phe
            420                 425                 430

Gly Val Pro Arg Glu Ala Val Asp Pro Leu Met Arg Arg Ala Ala Lys
        435                 440                 445

Thr Ile Asn Phe Gly Val Leu Tyr Gly Met Ser Ala His Arg Leu Ser
    450                 455                 460

Gln Glu Leu Ala Ile Pro Tyr Glu Glu Ala Gln Ala Phe Ile Glu Arg
465                 470                 475                 480

Tyr Phe Gln Ser Phe Pro Lys Val Arg Ala Trp Ile Glu Lys Thr Leu
                485                 490                 495

Glu Glu Gly Arg Arg Arg Gly Tyr Val Glu Thr Leu Phe Gly Arg Arg
            500                 505                 510

Arg Tyr Val Pro Asp Leu Glu Ala Arg Val Lys Ser Val Arg Glu Ala
        515                 520                 525

Ala Glu Arg Met Ala Phe Asn Met Pro Val Gln Gly Thr Ala Ala Asp
    530                 535                 540

Leu Met Lys Leu Ala Met Val Lys Leu Phe Pro Arg Leu Glu Glu Met
545                 550                 555                 560

Gly Ala Arg Met Leu Leu Gln Val His Asp Glu Leu Val Leu Glu Ala
                565                 570                 575

Pro Lys Glu Arg Ala Glu Ala Val Ala Arg Leu Ala Lys Glu Val Met
            580                 585                 590

Glu Gly Val Tyr Pro Leu Ala Val Pro Leu Glu Val Glu Val Gly Ile
        595                 600                 605

Gly Glu Asp Trp Leu Ser Ala Lys Glu Gly Ile Asp Gly Arg Gly Gly
    610                 615                 620

Gly Gly His His His His His His
625                 630


<210> SEQ ID NO 5
<211> LENGTH: 2763
<212> TYPE: DNA
<213> ORGANISM: Artificial Sequence
<220> FEATURE:
<223> OTHER INFORMATION: Description of Artificial Sequence:fusion
      protein Ssod7d/full-length Taq
<220> FEATURE:
<221> NAME/KEY: CDS
<222> LOCATION: (1)..(2763)
<223> OTHER INFORMATION: Ssod7d/full-length Taq

<400> SEQUENCE: 5

atgattacga attcgagcgc aaccgtaaag ttcaagtaca aaggcgaaga aaaagaggta      60

gacatctcca agatcaagaa agtatggcgt gtgggcaaga tgatctcctt cacctacgac     120

gagggcggtg gcaagaccgg ccgtggtgcg gtaagcgaaa aggacgcgcc gaaggagctg     180

ctgcagatgc tggagaagca gaaaaagggc ggcggtgtca ctagtgggat gctgcccctc     240

tttgagccca agggccgggt cctcctggtg gacggccacc acctggccta ccgcaccttc     300

cacgccctga agggcctcac caccagccgg ggggagccgg tgcaggcggt ctacggcttc     360

gccaagagcc tcctcaaggc cctcaaggag gacggggacg cggtgatcgt ggtctttgac     420

gccaaggccc cctccttccg ccacgaggcc tacggggggt acaaggcggg ccgggccccc     480

acgccagagg actttccccg gcaactcgcc ctcatcaagg agctggtgga cctcctgggg     540

ctggcgcgcc tcgaggtccc gggctacgag gcggacgacg tcctggccag cctggccaag     600

aaggcggaaa aggagggcta cgaggtccgc atcctcaccg ccgacaaaga cctttaccag     660
```

-continued

```
ctcctttccg accgcatcca cgtcctccac cccgaggggt acctcatcac cccggcctgg    720

ctttgggaaa agtacggcct gaggcccgac cagtgggccg actaccgggc cctgaccggg    780

gacgagtccg acaaccttcc cggggtcaag ggcatcgggg agaagacggc gaggaagctt    840

ctggaggagt gggggagcct ggaagccctc ctcaagaacc tggaccggct gaagcccgcc    900

atccgggaga agatcctggc ccacatggac gatctgaagc tctcctggga cctggccaag    960

gtgcgcaccg acctgcccct ggaggtggac ttcgccaaaa ggcgggagcc cgaccgggag   1020

aggcttaggg cctttctgga gaggcttgag tttggcagcc tcctccacga gttcggcctt   1080

ctggaaagcc ccaaggccct ggaggaggcc ccctggcccc cgccggaagg ggccttcgtg   1140

ggctttgtgc tttcccgcaa ggagcccatg tgggccgatc ttctggccct ggccgccgcc   1200

agggggggcc gggtccaccg ggcccccgag ccttataaag ccctcaggga cctgaaggag   1260

gcgcgggggc ttctcgccaa agacctgagc gttctggccc tgagggaagg ccttggcctc   1320

ccgcccggcg acgaccccat gctcctcgcc tacctcctgg acccttccaa caccaccccc   1380

gagggggtgg cccggcgcta cggcggggag tggacggagg aggcggggga gcgggccgcc   1440

ctttccgaga ggctcttcgc caacctgtgg gggaggcttg agggggagga gaggctcctt   1500

tggctttacc gggaggtgga gaggcccctt tccgctgtcc tggcccacat ggaggccacg   1560

ggggtgcgcc tggacgtggc ctatctcagg gccttgtccc tggaggtggc cgaggagatc   1620

gcccgcctcg aggccgaggt cttccgcctg gccggccacc ccttcaacct caactcccgg   1680

gaccagctgg aaagggtcct ctttgacgag ctagggcttc ccgccatcgg caagacggag   1740

aagaccggca agcgctccac cagcgccgcc gtcctggagg ccctccgcga ggcccacccc   1800

atcgtggaga agatcctgca gtaccgggag ctcaccaagc tgaagagcac ctacattgac   1860

cccttgccgg acctcatcca ccccaggacg ggccgcctcc acacccgctt caaccagacg   1920

gccacggcca cgggcaggct aagtagctcc gatcccaacc tccagaacat ccccgtccgc   1980

accccgcttg ggcagaggat ccgccgggcc ttcatcgccg aggaggggtg gctattggtg   2040

gccctggact atagccagat agagctcagg gtgctggccc acctctccgg cgacgagaac   2100

ctgatccggg tcttccagga ggggcgggac atccacacgg agaccgccag ctggatgttc   2160

ggcgtccccc gggaggccgt ggacccccctg atgcgccggg cggccaagac catcaacttc   2220

ggggtcctct acggcatgtc ggcccaccgc ctctcccagg agctagccat cccttacgag   2280

gaggcccagg ccttcattga gcgctacttt cagagcttcc ccaaggtgcg ggcctggatt   2340

gagaagaccc tggaggaggg caggaggcgg gggtacgtgg agaccctctt cggccgccgc   2400

cgctacgtgc cagacctaga ggcccgggtg aagagcgtgc gggaggcggc cgagcgcatg   2460

gccttcaaca tgcccgtcca gggcaccgcc gccgacctca tgaagctggc tatggtgaag   2520

ctcttcccca ggctggagga aatgggggcc aggatgctcc ttcaggtcca cgacgagctg   2580

gtcctcgagg ccccaaaaga gagggcggag gccgtggccc ggctggccaa ggaggtcatg   2640

gagggggtgt atcccctggc cgtgcccctg gaggtggagg tggggatagg ggaggactgg   2700

ctctccgcca aggagggcat tgatggccgc ggcggaggcg ggcatcatca tcatcatcat   2760

taa                                                                 2763
```

<210> SEQ ID NO 6
<211> LENGTH: 920
<212> TYPE: PRT
<213> ORGANISM: Artificial Sequence

```
<220> FEATURE:
<223> OTHER INFORMATION: Description of Artificial Sequence:fusion
      protein Ssod7d/full-length Taq

<400> SEQUENCE: 6

Met Ile Thr Asn Ser Ser Ala Thr Val Lys Phe Lys Tyr Lys Gly Glu
  1               5                  10                  15

Glu Lys Glu Val Asp Ile Ser Lys Ile Lys Lys Val Trp Arg Val Gly
             20                  25                  30

Lys Met Ile Ser Phe Thr Tyr Asp Glu Gly Gly Gly Lys Thr Gly Arg
         35                  40                  45

Gly Ala Val Ser Glu Lys Asp Ala Pro Lys Glu Leu Leu Gln Met Leu
     50                  55                  60

Glu Lys Gln Lys Lys Gly Gly Gly Val Thr Ser Gly Met Leu Pro Leu
 65                  70                  75                  80

Phe Glu Pro Lys Gly Arg Val Leu Leu Val Asp Gly His His Leu Ala
                 85                  90                  95

Tyr Arg Thr Phe His Ala Leu Lys Gly Leu Thr Thr Ser Arg Gly Glu
            100                 105                 110

Pro Val Gln Ala Val Tyr Gly Phe Ala Lys Ser Leu Leu Lys Ala Leu
        115                 120                 125

Lys Glu Asp Gly Asp Ala Val Ile Val Val Phe Asp Ala Lys Ala Pro
    130                 135                 140

Ser Phe Arg His Glu Ala Tyr Gly Gly Tyr Lys Ala Gly Arg Ala Pro
145                 150                 155                 160

Thr Pro Glu Asp Phe Pro Arg Gln Leu Ala Leu Ile Lys Glu Leu Val
                165                 170                 175

Asp Leu Leu Gly Leu Ala Arg Leu Glu Val Pro Gly Tyr Glu Ala Asp
            180                 185                 190

Asp Val Leu Ala Ser Leu Ala Lys Lys Ala Glu Lys Glu Gly Tyr Glu
        195                 200                 205

Val Arg Ile Leu Thr Ala Asp Lys Asp Leu Tyr Gln Leu Leu Ser Asp
    210                 215                 220

Arg Ile His Val Leu His Pro Glu Gly Tyr Leu Ile Thr Pro Ala Trp
225                 230                 235                 240

Leu Trp Glu Lys Tyr Gly Leu Arg Pro Asp Gln Trp Ala Asp Tyr Arg
                245                 250                 255

Ala Leu Thr Gly Asp Glu Ser Asp Asn Leu Pro Gly Val Lys Gly Ile
            260                 265                 270

Gly Glu Lys Thr Ala Arg Lys Leu Leu Glu Glu Trp Gly Ser Leu Glu
        275                 280                 285

Ala Leu Leu Lys Asn Leu Asp Arg Leu Lys Pro Ala Ile Arg Glu Lys
    290                 295                 300

Ile Leu Ala His Met Asp Asp Leu Lys Leu Ser Trp Asp Leu Ala Lys
305                 310                 315                 320

Val Arg Thr Asp Leu Pro Leu Glu Val Asp Phe Ala Lys Arg Arg Glu
                325                 330                 335

Pro Asp Arg Glu Arg Leu Arg Ala Phe Leu Glu Arg Leu Glu Phe Gly
            340                 345                 350

Ser Leu Leu His Glu Phe Gly Leu Leu Glu Ser Pro Lys Ala Leu Glu
        355                 360                 365

Glu Ala Pro Trp Pro Pro Pro Glu Gly Ala Phe Val Gly Phe Val Leu
    370                 375                 380
```

-continued

```
Ser Arg Lys Glu Pro Met Trp Ala Asp Leu Leu Ala Leu Ala Ala Ala
385                 390                 395                 400

Arg Gly Gly Arg Val His Arg Ala Pro Glu Pro Tyr Lys Ala Leu Arg
                405                 410                 415

Asp Leu Lys Glu Ala Arg Gly Leu Leu Ala Lys Asp Leu Ser Val Leu
            420                 425                 430

Ala Leu Arg Glu Gly Leu Gly Leu Pro Pro Gly Asp Asp Pro Met Leu
        435                 440                 445

Leu Ala Tyr Leu Leu Asp Pro Ser Asn Thr Thr Pro Glu Gly Val Ala
    450                 455                 460

Arg Arg Tyr Gly Gly Glu Trp Thr Glu Glu Ala Gly Glu Arg Ala Ala
465                 470                 475                 480

Leu Ser Glu Arg Leu Phe Ala Asn Leu Trp Gly Arg Leu Glu Gly Glu
                485                 490                 495

Glu Arg Leu Leu Trp Leu Tyr Arg Glu Val Glu Arg Pro Leu Ser Ala
            500                 505                 510

Val Leu Ala His Met Glu Ala Thr Gly Val Arg Leu Asp Val Ala Tyr
        515                 520                 525

Leu Arg Ala Leu Ser Leu Glu Val Ala Glu Glu Ile Ala Arg Leu Glu
    530                 535                 540

Ala Glu Val Phe Arg Leu Ala Gly His Pro Phe Asn Leu Asn Ser Arg
545                 550                 555                 560

Asp Gln Leu Glu Arg Val Leu Phe Asp Glu Leu Gly Leu Pro Ala Ile
                565                 570                 575

Gly Lys Thr Glu Lys Thr Gly Lys Arg Ser Thr Ser Ala Ala Val Leu
            580                 585                 590

Glu Ala Leu Arg Glu Ala His Pro Ile Val Glu Lys Ile Leu Gln Tyr
        595                 600                 605

Arg Glu Leu Thr Lys Leu Lys Ser Thr Tyr Ile Asp Pro Leu Pro Asp
    610                 615                 620

Leu Ile His Pro Arg Thr Gly Arg Leu His Thr Arg Phe Asn Gln Thr
625                 630                 635                 640

Ala Thr Ala Thr Gly Arg Leu Ser Ser Ser Asp Pro Asn Leu Gln Asn
                645                 650                 655

Ile Pro Val Arg Thr Pro Leu Gly Gln Arg Ile Arg Arg Ala Phe Ile
            660                 665                 670

Ala Glu Glu Gly Trp Leu Leu Val Ala Leu Asp Tyr Ser Gln Ile Glu
        675                 680                 685

Leu Arg Val Leu Ala His Leu Ser Gly Asp Glu Asn Leu Ile Arg Val
    690                 695                 700

Phe Gln Glu Gly Arg Asp Ile His Thr Glu Thr Ala Ser Trp Met Phe
705                 710                 715                 720

Gly Val Pro Arg Glu Ala Val Asp Pro Leu Met Arg Arg Ala Ala Lys
                725                 730                 735

Thr Ile Asn Phe Gly Val Leu Tyr Gly Met Ser Ala His Arg Leu Ser
            740                 745                 750

Gln Glu Leu Ala Ile Pro Tyr Glu Glu Ala Gln Ala Phe Ile Glu Arg
        755                 760                 765

Tyr Phe Gln Ser Phe Pro Lys Val Arg Ala Trp Ile Glu Lys Thr Leu
    770                 775                 780

Glu Glu Gly Arg Arg Arg Gly Tyr Val Glu Thr Leu Phe Gly Arg Arg
785                 790                 795                 800
```

-continued

```
Arg Tyr Val Pro Asp Leu Glu Ala Arg Val Lys Ser Val Arg Glu Ala
                805                 810                 815

Ala Glu Arg Met Ala Phe Asn Met Pro Val Gln Gly Thr Ala Ala Asp
            820                 825                 830

Leu Met Lys Leu Ala Met Val Lys Leu Phe Pro Arg Leu Glu Glu Met
        835                 840                 845

Gly Ala Arg Met Leu Leu Gln Val His Asp Glu Leu Val Leu Glu Ala
    850                 855                 860

Pro Lys Glu Arg Ala Glu Ala Val Ala Arg Leu Ala Lys Glu Val Met
865                 870                 875                 880

Glu Gly Val Tyr Pro Leu Ala Val Pro Leu Glu Val Glu Val Gly Ile
                885                 890                 895

Gly Glu Asp Trp Leu Ser Ala Lys Glu Gly Ile Asp Gly Arg Gly Gly
            900                 905                 910

Gly Gly His His His His His His
        915                 920


<210> SEQ ID NO 7
<211> LENGTH: 2535
<212> TYPE: DNA
<213> ORGANISM: Artificial Sequence
<220> FEATURE:
<223> OTHER INFORMATION: Description of Artificial Sequence:fusion
      protein Pfu-Ssod7d
<220> FEATURE:
<221> NAME/KEY: CDS
<222> LOCATION: (1)..(2535)
<223> OTHER INFORMATION: Pfu-Ssod7d

<400> SEQUENCE: 7

atgattttag atgtggatta cataactgaa gaaggaaaac ctgttattag gctattcaaa      60

aaagagaacg gaaaatttaa gatagagcat gatagaactt ttagaccata catttacgct     120

cttctcaggg atgattcaaa gattgaagaa gttaagaaaa taacggggga aaggcatgga     180

aagattgtga gaattgttga tgtagagaag gttgagaaaa agtttctcgg caagcctatt     240

accgtgtgga aactttattt ggaacatccc caagatgttc ccactattag agaaaaagtt     300

agagaacatc cagcagttgt ggacatcttc gaatacgata ttccatttgc aaagagatac     360

ctcatcgaca aaggcctaat accaatggag ggggaagaag agctaaagat tcttgccttc     420

gatatagaaa ccctctatca cgaaggagaa gagtttggaa aaggcccaat tataatgatt     480

agttatgcag atgaaaatga agcaaaggtg attacttgga aaaacataga tcttccatac     540

gttgaggttg tatcaagcga gagagagatg ataaagagat ttctcaggat tatcagggag     600

aaggatcctg acattatagt tacttataat ggagactcat tcgacttccc atatttagcg     660

aaaagggcag aaaaacttgg gattaaatta accattggaa gagatggaag cgagcccaag     720

atgcagagaa taggcgatat gacggctgta gaagtcaagg gaagaataca tttcgacttg     780

tatcatgtaa taacaaggac aataaatctc ccaacataca cactagaggc tgtatatgaa     840

gcaatttttg gaaagccaaa ggagaaggta tacgccgacg agatagcaaa agcctgggaa     900

agtggagaga accttgagag agttgccaaa tactcgatgg aagatgcaaa ggcaacttat     960

gaactcggga aagaattcct tccaatggaa attcagcttt caagattagt tggacaacct    1020

ttatgggatg tttcaaggtc aagcacaggg aaccttgtag agtggttctt acttaggaaa    1080

gcctacgaaa gaaacgaagt agctccaaac aagccaagtg aagaggagta tcaaagaagg    1140

ctcagggaga gctacacagg tggattcgtt aaagagccag aaaaggggtt gtgggaaaac    1200
```

-continued

```
atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg ggaaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca ttgagaacca ggttcttcca   2220

gcggtactta ggatattgga gggatttgga tacagaaagg aagacctcag ataccaaaag   2280

acaagacaag tcggcctaac ttcctggctt aacattaaaa aatccggtac cggcggtggc   2340

ggtgcaaccg taaagttcaa gtacaaaggc gaagaaaaag aggtagacat ctccaagatc   2400

aagaaagtat ggcgtgtggg caagatgatc tccttcacct acgacgaggg cggtggcaag   2460

accggccgtg gtgcggtaag cgaaaaggac gcgccgaagg agctgctgca gatgctggag   2520

aagcagaaaa agtga                                                    2535
```

<210> SEQ ID NO 8
<211> LENGTH: 844
<212> TYPE: PRT
<213> ORGANISM: Artificial Sequence
<220> FEATURE:
<223> OTHER INFORMATION: Description of Artificial Sequence:fusion protein Pfu-Ssod7d

<400> SEQUENCE: 8

```
Met Ile Leu Asp Val Asp Tyr Ile Thr Glu Glu Gly Lys Pro Val Ile
  1               5                  10                  15

Arg Leu Phe Lys Lys Glu Asn Gly Lys Phe Lys Ile Glu His Asp Arg
             20                  25                  30

Thr Phe Arg Pro Tyr Ile Tyr Ala Leu Leu Arg Asp Asp Ser Lys Ile
         35                  40                  45

Glu Glu Val Lys Lys Ile Thr Gly Glu Arg His Gly Lys Ile Val Arg
     50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
            100                 105                 110
```

-continued

```
Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525
```

-continued

```
Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser Gly Thr Gly Gly Gly Gly Ala Thr Val
    770                 775                 780

Lys Phe Lys Tyr Lys Gly Glu Glu Lys Glu Val Asp Ile Ser Lys Ile
785                 790                 795                 800

Lys Lys Val Trp Arg Val Gly Lys Met Ile Ser Phe Thr Tyr Asp Glu
                805                 810                 815

Gly Gly Gly Lys Thr Gly Arg Gly Ala Val Ser Glu Lys Asp Ala Pro
            820                 825                 830

Lys Glu Leu Leu Gln Met Leu Glu Lys Gln Lys Lys
        835                 840
```

```
<210> SEQ ID NO 9
<211> LENGTH: 1904
<212> TYPE: DNA
<213> ORGANISM: Artificial Sequence
<220> FEATURE:
<223> OTHER INFORMATION: Description of Artificial Sequence:fusion
      protein Sac7d-deltaTaq
<220> FEATURE:
<221> NAME/KEY: CDS
<222> LOCATION: (1)..(1904)
<223> OTHER INFORMATION: Sac7d-deltaTaq

<400> SEQUENCE: 9

atgattacga attcgacggt gaaggtaaag ttcaagtata agggtgaaga gaaagaagta      60

gacacttcaa agataaagaa ggtttggaga gtaggcaaaa tggtgtcctt tacctatgac     120
```

-continued

```
gacaatggta agacaggtag aggagctgta agcgagaaag atgctccaaa agaattatta    180

gacatgttag caagagcaga aagagagaag aaaggcggcg gtgtcactag tcccaaggcc    240

ctggaggagg ccccctggcc cccgccggaa ggggccttcg tgggctttgt gctttcccgc    300

aaggagccca tgtgggccga tcttctggcc ctggccgccg ccaggggggg ccgggtccac    360

cgggcccccg agccttataa agccctcagg gacctgaagg aggcgcgggg gcttctcgcc    420

aaagacctga gcgttctggc cctgagggaa ggccttggcc tcccgcccgg cgacgacccc    480

atgctcctcg cctacctcct ggacccttcc aacaccaccc ccgagggggt ggcccggcgc    540

tacggcgggg agtggacgga ggaggcgggg gagcgggccg ccctttccga gaggctcttc    600

gccaacctgt gggggaggct tgagggggag gagaggctcc tttggcttta ccgggaggtg    660

gagaggcccc tttccgctgt cctggcccac atggaggcca cgggggtgcg cctggacgtg    720

gcctatctca gggccttgtc cctggaggtg gccgaggaga tcgcccgcct cgaggccggg    780

tcttccgcct ggccggccac cccttcaacc tcaactcccg ggaccagctg gaaagggtcc    840

tctttgacga gctagggctt cccgccatcg gcaagacgga gaagaccggc aagcgctcca    900

ccagcgccgc cgtcctggag gccctccgcg aggcccaccc catcgtggag aagatcctgc    960

agtaccggga gctcaccaag ctgaagagca cctacattga ccccttgccg gacctcatcc   1020

accccaggac gggccgcctc cacacccgct tcaaccagac ggccacggcc acgggcaggc   1080

taagtagctc cgatcccaac ctccagaaca tccccgtccg caccccgctt gggcagagga   1140

tccgccgggc cttcatcgcc gaggaggggt ggctattggt ggccctggac tatagccaga   1200

tagagctcag ggtgctggcc cacctctccg gcgacgagaa cctgatccgg gtcttccagg   1260

aggggcggga catccacacg gagaccgcca gctggatgtt cggcgtcccc cgggaggccg   1320

tggacccccct gatgcgccgg gcggccaaga ccatcaactt cggggtcctc tacggcatgt   1380

cggcccaccg cctctcccag gagctagcca tcccttacga ggaggcccag gccttcattg   1440

agcgctactt tcagagcttc cccaaggtgc gggcctggat tgagaagacc ctggaggagg   1500

gcaggaggcg gggtacgtg gagaccctct tcggccgccg ccgctacgtg ccagacctag   1560

aggcccgggt gaagagcgtg cgggaggcgg ccgagcgcat ggccttcaac atgcccgtcc   1620

agggcaccgc cgccgacctc atgaagctgg ctatggtgaa gctcttcccc aggctggagg   1680

aaatgggggc caggatgctc cttcaggtcc acgacgagct ggtcctcgag gccccaaaag   1740

agagggcgga ggccgtggcc cggctggcca aggaggtcat ggaggggtg tatcccctgg   1800

ccgtgcccct ggaggtggag gtggggatag gggaggactg gctctccgcc aaggagggca   1860

ttgatggccg cggcggaggc gggcatcatc atcatcatca ttaa                    1904


<210> SEQ ID NO 10
<211> LENGTH: 634
<212> TYPE: PRT
<213> ORGANISM: Artificial Sequence
<220> FEATURE:
<223> OTHER INFORMATION: Description of Artificial Sequence:fusion
      protein Sac7d-deltaTaq

<400> SEQUENCE: 10

Met Ile Thr Asn Ser Thr Val Lys Val Lys Phe Lys Tyr Lys Gly Glu
  1               5                  10                  15

Glu Lys Glu Val Asp Thr Ser Lys Ile Lys Lys Val Trp Arg Val Gly
             20                  25                  30

Lys Met Val Ser Phe Thr Tyr Asp Asp Asn Gly Lys Thr Gly Arg Gly
         35                  40                  45
```

-continued

```
Ala Val Ser Glu Lys Asp Ala Pro Lys Glu Leu Leu Asp Met Leu Ala
     50                  55                  60

Arg Ala Glu Arg Glu Lys Lys Gly Gly Gly Val Thr Ser Pro Lys Ala
 65                  70                  75                  80

Leu Glu Glu Ala Pro Trp Pro Pro Pro Glu Gly Ala Phe Val Gly Phe
                 85                  90                  95

Val Leu Ser Arg Lys Glu Pro Met Trp Ala Asp Leu Leu Ala Leu Ala
            100                 105                 110

Ala Ala Arg Gly Gly Arg Val His Arg Ala Pro Glu Pro Tyr Lys Ala
        115                 120                 125

Leu Arg Asp Leu Lys Glu Ala Arg Gly Leu Leu Ala Lys Asp Leu Ser
    130                 135                 140

Val Leu Ala Leu Arg Glu Gly Leu Gly Leu Pro Pro Gly Asp Asp Pro
145                 150                 155                 160

Met Leu Leu Ala Tyr Leu Leu Asp Pro Ser Asn Thr Thr Pro Glu Gly
                165                 170                 175

Val Ala Arg Arg Tyr Gly Gly Glu Trp Thr Glu Glu Ala Gly Glu Arg
            180                 185                 190

Ala Ala Leu Ser Glu Arg Leu Phe Ala Asn Leu Trp Gly Arg Leu Glu
        195                 200                 205

Gly Glu Glu Arg Leu Leu Trp Leu Tyr Arg Glu Val Glu Arg Pro Leu
    210                 215                 220

Ser Ala Val Leu Ala His Met Glu Ala Thr Gly Val Arg Leu Asp Val
225                 230                 235                 240

Ala Tyr Leu Arg Ala Leu Ser Leu Glu Val Ala Glu Glu Ile Ala Arg
                245                 250                 255

Leu Glu Ala Glu Val Phe Arg Leu Ala Gly His Pro Phe Asn Leu Asn
            260                 265                 270

Ser Arg Asp Gln Leu Glu Arg Val Leu Phe Asp Glu Leu Gly Leu Pro
        275                 280                 285

Ala Ile Gly Lys Thr Glu Lys Thr Gly Lys Arg Ser Thr Ser Ala Ala
    290                 295                 300

Val Leu Glu Ala Leu Arg Glu Ala His Pro Ile Val Glu Lys Ile Leu
305                 310                 315                 320

Gln Tyr Arg Glu Leu Thr Lys Leu Lys Ser Thr Tyr Ile Asp Pro Leu
                325                 330                 335

Pro Asp Leu Ile His Pro Arg Thr Gly Arg Leu His Thr Arg Phe Asn
            340                 345                 350

Gln Thr Ala Thr Ala Thr Gly Arg Leu Ser Ser Ser Asp Pro Asn Leu
        355                 360                 365

Gln Asn Ile Pro Val Arg Thr Pro Leu Gly Gln Arg Ile Arg Arg Ala
    370                 375                 380

Phe Ile Ala Glu Glu Gly Trp Leu Leu Val Ala Leu Asp Tyr Ser Gln
385                 390                 395                 400

Ile Glu Leu Arg Val Leu Ala His Leu Ser Gly Asp Glu Asn Leu Ile
                405                 410                 415

Arg Val Phe Gln Glu Gly Arg Asp Ile His Thr Glu Thr Ala Ser Trp
            420                 425                 430

Met Phe Gly Val Pro Arg Glu Ala Val Asp Pro Leu Met Arg Arg Ala
        435                 440                 445

Ala Lys Thr Ile Asn Phe Gly Val Leu Tyr Gly Met Ser Ala His Arg
    450                 455                 460
```

-continued

```
Leu Ser Gln Glu Leu Ala Ile Pro Tyr Glu Glu Ala Gln Ala Phe Ile
465                 470                 475                 480

Glu Arg Tyr Phe Gln Ser Phe Pro Lys Val Arg Ala Trp Ile Glu Lys
                485                 490                 495

Thr Leu Glu Glu Gly Arg Arg Arg Gly Tyr Val Glu Thr Leu Phe Gly
            500                 505                 510

Arg Arg Arg Tyr Val Pro Asp Leu Glu Ala Arg Val Lys Ser Val Arg
        515                 520                 525

Glu Ala Ala Glu Arg Met Ala Phe Asn Met Pro Val Gln Gly Thr Ala
    530                 535                 540

Ala Asp Leu Met Lys Leu Ala Met Val Lys Leu Phe Pro Arg Leu Glu
545                 550                 555                 560

Glu Met Gly Ala Arg Met Leu Leu Gln Val His Asp Glu Leu Val Leu
                565                 570                 575

Glu Ala Pro Lys Glu Arg Ala Glu Ala Val Ala Arg Leu Ala Lys Glu
            580                 585                 590

Val Met Glu Gly Val Tyr Pro Leu Ala Val Pro Leu Glu Val Glu Val
        595                 600                 605

Gly Ile Gly Glu Asp Trp Leu Ser Ala Lys Glu Gly Ile Asp Gly Arg
    610                 615                 620

Gly Gly Gly Gly His His His His His His
625                 630
```

<210> SEQ ID NO 11
<211> LENGTH: 1965
<212> TYPE: DNA
<213> ORGANISM: Artificial Sequence
<220> FEATURE:
<223> OTHER INFORMATION: Description of Artificial Sequence:fusion
      protein PL-deltaTaq
<220> FEATURE:
<221> NAME/KEY: CDS
<222> LOCATION: (1)..(1965)
<223> OTHER INFORMATION: PL-deltaTaq

<400> SEQUENCE: 11

```
atgattacga attcgaagaa aaagaaaaag aaaaagcgta agaaacgcaa aaagaaaaag      60

aaaggcggcg gtgtcactag tggcgcaacc gtaaagttca agtacaaagg cgaagaaaaa     120

gaggtagaca tctccaagat caagaaagta tggcgtgtgg gcaagatgat ctccttcacc     180

tacgacgagg gcggtggcaa gaccggccgt ggtgcggtaa gcgaaaagga cgcgccgaag     240

gagctgctgc agatgctgga gaagcagaaa aagggcggcg gtgtcaccag tcccaaggcc     300

ctggaggagg ccccctggcc cccgccggaa ggggccttcg tgggctttgt gctttcccgc     360

aaggagccca tgtgggccga tcttctggcc ctggccgccg ccaggggggg ccgggtccac     420

cgggcccccg agccttataa agccctcagg gacctgaagg aggcgcgggg gcttctcgcc     480

aaagacctga gcgttctggc cctgagggaa ggccttggcc tcccgcccgg cgacgacccc     540

atgctcctcg cctacctcct ggacccttcc aacaccaccc ccgagggggt ggcccggcgc     600

tacggcgggg agtggacgga ggaggcgggg gagcgggccg ccctttccga gaggctcttc     660

gccaacctgt gggggaggct tgagggggag gagaggctcc tttggcttta ccgggaggtg     720

gagaggcccc tttccgctgt cctggcccac atggaggcca cgggggtgcg cctggacgtg     780

gcctatctca gggccttgtc cctggaggtg gccgaggaga tcgcccgcct cgaggccgag     840

gtcttccgcc tggccggcca ccccttcaac ctcaactccc gggaccagct ggaaagggtc     900

ctctttgacg agctagggct tcccgccatc ggcaagacgg agaagaccgg caagcgctcc     960
```

```
accagcgccg ccgtcctgga ggccctccgc gaggcccacc ccatcgtgga gaagatcctg   1020

cagtaccggg agctcaccaa gctgaagagc acctacattg acccccttgcc ggacctcatc   1080

caccccagga cgggccgcct ccacacccgc ttcaaccaga cggccacggc cacgggcagg   1140

ctaagtagct ccgatcccaa cctccagaac atccccgtcc gcaccccgct tgggcagagg   1200

atccgccggg ccttcatcgc cgaggagggg tggctattgg tggccctgga ctatagccag   1260

atagagctca gggtgctggc ccacctctcc ggcgacgaga acctgatccg ggtcttccag   1320

gaggggcggg acatccacac ggagaccgcc agctggatgt tcggcgtccc ccgggaggcc   1380

gtggaccccc tgatgcgccg ggcggccaag accatcaact tcggggtcct ctacggcatg   1440

tcggcccacc gcctctccca ggagctagcc atcccttacg aggaggccca ggccttcatt   1500

gagcgctact ttcagagctt ccccaaggtg cgggcctgga ttgagaagac cctggaggag   1560

ggcaggaggc gggggtacgt ggagaccctc ttcggccgcc gccgctacgt gccagaccta   1620

gaggcccggg tgaagagcgt gcgggaggcg gccgagcgca tggccttcaa catgcccgtc   1680

cagggcaccg ccgccgacct catgaagctg gctatggtga agctcttccc caggctggag   1740

gaaatggggg ccaggatgct ccttcaggtc cacgacgagc tggtcctcga ggccccaaaa   1800

gagagggcgg aggccgtggc ccggctggcc aaggaggtca tggagggggt gtatcccctg   1860

gccgtgcccc tggaggtgga ggtggggata ggggaggact ggctctccgc caaggagggc   1920

attgatggcc gcggcggagg cgggcatcat catcatcatc attaa                   1965
```

<210> SEQ ID NO 12
<211> LENGTH: 654
<212> TYPE: PRT
<213> ORGANISM: Artificial Sequence
<220> FEATURE:
<223> OTHER INFORMATION: Description of Artificial Sequence:fusion protein PL-deltaTaq

<400> SEQUENCE: 12

```
Met Ile Thr Asn Ser Lys Lys Lys Lys Lys Lys Lys Arg Lys Lys Arg
  1               5                  10                  15

Lys Lys Lys Lys Lys Gly Gly Gly Val Thr Ser Gly Ala Thr Val Lys
             20                  25                  30

Phe Lys Tyr Lys Gly Glu Glu Lys Glu Val Asp Ile Ser Lys Ile Lys
         35                  40                  45

Lys Val Trp Arg Val Gly Lys Met Ile Ser Phe Thr Tyr Asp Glu Gly
     50                  55                  60

Gly Gly Lys Thr Gly Arg Gly Ala Val Ser Glu Lys Asp Ala Pro Lys
 65                  70                  75                  80

Glu Leu Leu Gln Met Leu Glu Lys Gln Lys Lys Gly Gly Gly Val Thr
                 85                  90                  95

Ser Pro Lys Ala Leu Glu Glu Ala Pro Trp Pro Pro Pro Glu Gly Ala
            100                 105                 110

Phe Val Gly Phe Val Leu Ser Arg Lys Glu Pro Met Trp Ala Asp Leu
        115                 120                 125

Leu Ala Leu Ala Ala Ala Arg Gly Gly Arg Val His Arg Ala Pro Glu
    130                 135                 140

Pro Tyr Lys Ala Leu Arg Asp Leu Lys Glu Ala Arg Gly Leu Leu Ala
145                 150                 155                 160

Lys Asp Leu Ser Val Leu Ala Leu Arg Glu Gly Leu Gly Leu Pro Pro
                165                 170                 175
```

-continued

```
Gly Asp Asp Pro Met Leu Leu Ala Tyr Leu Leu Asp Pro Ser Asn Thr
            180                 185                 190

Thr Pro Glu Gly Val Ala Arg Arg Tyr Gly Gly Glu Trp Thr Glu Glu
        195                 200                 205

Ala Gly Glu Arg Ala Ala Leu Ser Glu Arg Leu Phe Ala Asn Leu Trp
    210                 215                 220

Gly Arg Leu Glu Gly Glu Glu Arg Leu Leu Trp Leu Tyr Arg Glu Val
225                 230                 235                 240

Glu Arg Pro Leu Ser Ala Val Leu Ala His Met Glu Ala Thr Gly Val
                245                 250                 255

Arg Leu Asp Val Ala Tyr Leu Arg Ala Leu Ser Leu Glu Val Ala Glu
            260                 265                 270

Glu Ile Ala Arg Leu Glu Ala Glu Val Phe Arg Leu Ala Gly His Pro
        275                 280                 285

Phe Asn Leu Asn Ser Arg Asp Gln Leu Glu Arg Val Leu Phe Asp Glu
    290                 295                 300

Leu Gly Leu Pro Ala Ile Gly Lys Thr Glu Lys Thr Gly Lys Arg Ser
305                 310                 315                 320

Thr Ser Ala Ala Val Leu Glu Ala Leu Arg Glu Ala His Pro Ile Val
                325                 330                 335

Glu Lys Ile Leu Gln Tyr Arg Glu Leu Thr Lys Leu Lys Ser Thr Tyr
            340                 345                 350

Ile Asp Pro Leu Pro Asp Leu Ile His Pro Arg Thr Gly Arg Leu His
        355                 360                 365

Thr Arg Phe Asn Gln Thr Ala Thr Ala Thr Gly Arg Leu Ser Ser Ser
    370                 375                 380

Asp Pro Asn Leu Gln Asn Ile Pro Val Arg Thr Pro Leu Gly Gln Arg
385                 390                 395                 400

Ile Arg Arg Ala Phe Ile Ala Glu Glu Gly Trp Leu Leu Val Ala Leu
                405                 410                 415

Asp Tyr Ser Gln Ile Glu Leu Arg Val Leu Ala His Leu Ser Gly Asp
            420                 425                 430

Glu Asn Leu Ile Arg Val Phe Gln Glu Gly Arg Asp Ile His Thr Glu
        435                 440                 445

Thr Ala Ser Trp Met Phe Gly Val Pro Arg Glu Ala Val Asp Pro Leu
    450                 455                 460

Met Arg Arg Ala Ala Lys Thr Ile Asn Phe Gly Val Leu Tyr Gly Met
465                 470                 475                 480

Ser Ala His Arg Leu Ser Gln Glu Leu Ala Ile Pro Tyr Glu Glu Ala
                485                 490                 495

Gln Ala Phe Ile Glu Arg Tyr Phe Gln Ser Phe Pro Lys Val Arg Ala
            500                 505                 510

Trp Ile Glu Lys Thr Leu Glu Glu Gly Arg Arg Arg Gly Tyr Val Glu
        515                 520                 525

Thr Leu Phe Gly Arg Arg Arg Tyr Val Pro Asp Leu Glu Ala Arg Val
    530                 535                 540

Lys Ser Val Arg Glu Ala Ala Glu Arg Met Ala Phe Asn Met Pro Val
545                 550                 555                 560

Gln Gly Thr Ala Ala Asp Leu Met Lys Leu Ala Met Val Lys Leu Phe
                565                 570                 575

Pro Arg Leu Glu Glu Met Gly Ala Arg Met Leu Leu Gln Val His Asp
            580                 585                 590
```

-continued

```
Glu Leu Val Leu Glu Ala Pro Lys Glu Arg Ala Glu Ala Val Ala Arg
        595                 600                 605

Leu Ala Lys Glu Val Met Glu Gly Val Tyr Pro Leu Ala Val Pro Leu
    610                 615                 620

Glu Val Glu Val Gly Ile Gly Glu Asp Trp Leu Ser Ala Lys Glu Gly
625                 630                 635                 640

Ile Asp Gly Arg Gly Gly Gly Gly His His His His His His
                645                 650


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer L71F

<400> SEQUENCE: 13

cctgctctgc cgcttcacgc                                                  20


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:primer L71R

<400> SEQUENCE: 14

gcacagcggc tggctgagga                                                  20


<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:primer
      L18015F

<400> SEQUENCE: 15

tgacggagga taacgccagc ag                                               22


<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence:primer
      L23474R

<400> SEQUENCE: 16

gaaagacgat gggtcgctaa tacgc                                            25


<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:primer
      L18015F

<400> SEQUENCE: 17

tgacggagga taacgccagc ag                                               22
```

-continued

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence:primer L29930R

<400> SEQUENCE: 18
ggggttggag gtcaatgggt tc 22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:primer L30350F

<400> SEQUENCE: 19
cctgctctgc cgcttcacgc 20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence:primer L35121R

<400> SEQUENCE: 20
cacatggtac agcaagcctg gc 22

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence:primer L2089F

<400> SEQUENCE: 21
cccgtatctg ctgggatact ggc 23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:primer L7112R

<400> SEQUENCE: 22
cagcggtgct gactgaatca tgg 23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence:primer L30350F

<400> SEQUENCE: 23
cctgcctgcc gcttcacgc 19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:primer L40547R

<400> SEQUENCE: 24
ccaatacccg tttcatcgcg gc 22

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:primer H-Amelo-Y

<400> SEQUENCE: 25
ccacctcatc ctgggcacc 19

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:primerH-Amelo-YR

<400> SEQUENCE: 26
gcttgaggcc aaccatcaga gc 22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence:human beta-globin primer Bglbn536F

<400> SEQUENCE: 27
ggttggccaa tctactccca gg 22

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:human beta-globin primer Bglbn536R

<400> SEQUENCE: 28
gctcactcag tgtggcaaag 20

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:human beta-globin primer Bglbn1408R

<400> SEQUENCE: 29
gattagcaaa agggcctagc ttgg 24

-continued

```
<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 30

His His His His His His
  1               5


<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:
      anti-DYKDDDDK epitope tag

<400> SEQUENCE: 31

Asp Tyr Lys Asp Asp Asp Asp Lys
  1               5


<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:peptide
      linker

<400> SEQUENCE: 32

Gly Gly Val Thr
  1


<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence:peptide
      linker

<400> SEQUENCE: 33

Gly Thr Gly Gly Gly Gly
  1               5


<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence:lysine-rich
      peptide

<400> SEQUENCE: 34

Asn Ser Lys Lys Lys Lys Lys Lys Lys Arg Lys Lys Arg Lys Lys Lys
  1               5                  10                  15

Gly Gly Gly Val Thr
             20
```

NUCLEIC ACID MODIFYING ENZYMES

CROSS-REFERENCE TO RELATED APPLICATIONS

This application is a continuation-in-part of U.S. application Ser. No. 09/640,958, filed Aug. 16, 2000, now U.S. Pat. No. 6,627,424, which claims the benefit of U.S. Provisional Application Ser. No. 60/207,567, filed May 26, 2000. Each application is herein incorporated by reference.

FIELD OF THE INVENTION

This invention provides for an improved generation of novel nucleic acid modifying enzymes. The improvement is the joining of a sequence-non-specific nucleic-acid-binding domain to the enzyme in a manner that enhances the ability of the enzyme to bind and catalytically modify the nucleic acid.

BACKGROUND OF THE INVENTION

The efficiency of a nucleic acid modifying enzyme, i.e., the amount of modified product generated by the enzyme per binding event, can be enhanced by increasing the stability of the modifying enzyme/nucleic acid complex. The prior art has suggested that attachment of a high probability binding site, e.g., a positively charged binding tail, to a nucleic acid modifying enzyme can increase the frequency with which the modifying enzyme interacts with the nucleic acid (see, e.g., U.S. Pat. No. 5,474,911). The present invention now provides novel modifying enzymes in which the double-stranded conformation of the nucleic acid is stabilized and the efficiency of the enzyme increased by joining a sequence-non-specific double-stranded nucleic acid binding domain to the enzyme, or its catalytic domain. The modifying proteins that are processive in nature exhibit increased processivity when joined to a binding domain compared to the enzyme alone. Moreover, both processive and non-processive modifying enzymes exhibit increased efficiency at higher temperatures when joined to a typical binding domain described herein.

In one aspect, the invention provides fusion polymerases that provide an enhanced ability to perform long PCR, i.e., amplification of sequences of 5 kb or greater in length. Polymerase mixture to perform long PCR are known in the art. One difficulty with such mixtures is that long extension times are required for optimal yields of the expected products. Conventional recommendations are to allow extension times of 1 minute per kb. For a 10 kb product and using 40 cycles of amplification, the PCR requires approximately seven hours. Described herein are modified polymerase enzymes that exhibit an enhanced ability to perform long PCR compared to those polymerases and/or polymerase mixtures currently available. These modified enzymes, e.g., Pfu-Sso7d, incorporate a polymerase with error-correcting activity and a sequence-nonspecific double-stranded DNA-binding domain, and therefore provide the capability of PCR amplifying DNA larger than 5 kb without need to resort to polymerase mixtures. In addition, such modified enzymes can efficiently amplify a given fragment using shorter extension times than are required by conventional polymerase mixtures. Thus, use of the hybrid polymerases described herein instead of the conventional mixtures can greatly decrease the reaction time required to amplify large fragments, e.g. from about seven hours to about two hours.

SUMMARY OF THE INVENTION

The present invention provides a protein consisting of at least two heterologous domains wherein a first domain that is a sequence-non-specific double-stranded nucleic acid binding domain is joined to a second domain that is a catalytic nucleic acid modifying domain having a processive nature, where the presence of the sequence-non-specific double-stranded nucleic acid binding domain enhances the processive nature of the nucleic acid modifying domain compared to an identical protein not having a sequence-non-specific nucleic acid binding domain joined thereto. In one aspect of the invention, the nucleic acid modifying domain can have a polymerase activity, which can be thermally stable, e.g., a *Thermus* polymerase domain. In alternative embodiments, the catalytic domain is an RNA polymerase, a reverse transcriptase, a methylase, a 3' or 5' exonuclease, a gyrase, or a topoisomerase.

In a particular embodiment, a sequence-non-specific nucleic acid binding domain of the protein can specifically bind to polyclonal antibodies generated against Sac7d or Sso7d. Alternatively, the sequence-non-specific nucleic acid binding domain can contain a 50 amino acid subsequence that has 50% amino acid similarity to Sso7d. The nucleic acid binding domain can also be Sso7d.

In another embodiment, a protein of the invention contains a sequence-non-specific double-stranded nucleic acid binding domain that specifically binds to polyclonal antibodies generated against a PCNA homolog of *Pyrococcus furiosus*, or can be a PCNA homolog of *Pyrococcus furiosus*.

The invention also provides a protein consisting of at least two heterologous domains, wherein a first domain that is a sequence-non-specific double-stranded nucleic acid binding domain is joined to a second domain that is a catalytic nucleic-acid-modifying domain, where the presence of the sequence-non-specific nucleic-acid binding domain stabilizes the double-stranded conformation of a nucleic acid by at least 1° C. compared to an identical protein not having a sequence-non-specific nucleic acid binding domain joined thereto. The nucleic acid modifying domain of such a protein can have polymerase activity, which can be thermally stable. The nucleic-acid-modifying domain can also have RNA polymerase, reverse transcriptase, methylase, 3' or 5' exonuclease, gyrase, or topoisomerase activity.

In further embodiments, the sequence-non-specific nucleic-acid-binding domain can specifically bind to polyclonal antibodies generated against either Sac7d or Sso7d, frequently Sso7d, or contains a 50 amino acid subsequence containing 50% or 75% amino acid similarity to Sso7d. Often, the sequence-non-specific nucleic-acid-binding domain is Sso7d.

Proteins of the invention include a protein wherein the sequence-non-specific nucleic-acid-binding domain specifically binds to polyclonal antibodies generated against the PCNA homolog of *Pyrococcus furiosus*; often the binding domain is the PCNA homolog of *Pyrococcus furiosus*.

In another aspect, the invention provides methods of modifying nucleic acids using the proteins. One embodiment is a method of modifying a nucleic acid in an aqueous solution by: (i) contacting the nucleic acid with a protein comprising at least two heterologous domains, wherein a first domain that is a sequence-non-specific nucleic-acid-binding domain is joined to a second domain that is a catalytic nucleic-acid-modifying domain having a processive nature, where the sequence-non-specific nucleic-acid-binding domain:a. binds to double-stranded nucleic acid, and b. enhances the processivity of the enzyme compared to an identical enzyme not having the sequence non-specific nucleic-acid-binding domain fused to it, and wherein the solution is at a temperature and of a composition that permits the binding domain to bind to the nucleic acid and the enzyme to function in a catalytic manner; and (ii) permitting the catalytic domain to modify the nucleic acid in the solution.

In another aspect, the invention provides a method of modifying a nucleic acid by:(i) contacting the nucleic acid with an aqueous solution containing a protein having at least two heterologous domains, wherein a first domain that is a sequence-non-specific double-stranded nucleic-acid-binding domain is joined to a second domain that is a catalytic nucleic-acid-modifying domain, where the presence of the sequence-non-specific nucleic-acid-binding domain stabilizes the formation of a double-stranded nucleic acid compared to an otherwise identical protein not having the sequence-non-specific nucleic-acid-binding domain joined to it; and wherein the solution is at a temperature and of a composition that permits the binding domain to bind to the nucleic acid and the enzyme to function in a catalytic manner; and (ii) permitting the catalytic domain to modify the nucleic acid in the solution. The methods of modifying a nucleic acid can employ any of the protein embodiments described herein.

In further aspects, the invention provides a method of amplifying a 5 kb or longer subsequence of a target nucleic acid in an aqueous solution using a polymerase chain reaction, the method comprising:(i) contacting the target nucleic acid with a protein comprising at least two heterologous domains, wherein a first domain that is a sequence-non-specific nucleic-acid-binding domain is joined to a second domain that is a polymerase domain with error-correcting activity, where the sequence non-specific nucleic-acid-binding domain:(a) binds to double-stranded nucleic acid, and (b) enhances the processivity of the polymerase compared to an identical polymerase not having the sequence non-specific nucleic-acid-binding domain fused to it, and, wherein the solution is of a composition that permits the binding domain to bind to the target nucleic acid and the polymerase domain to extend a primer that is hybridized to the target nucleic acid sequence to a length of 5 kb or longer; (ii) incubating the solution using a polymerase chain reaction temperature profile that amplifies the 5 kb or longer subsequence. In one embodiment of the method, the nucleic-acid-modifying domain has thermally stable polymerase activity. Often, the nucleic-acid modifying domain comprises a Pyrococcus polymerase domain. In other embodiments of the method, the sequence-non-specific nucleic-acid-binding domain specifically binds to polyclonal antibodies generated against either Sac7d or Sso7d, contains a 50 amino acid subsequence containing 50% amino acid similarity to Sso7D, or specifically binds to polyclonal antibodies generated against Sso7d. In another embodiment, the sequence-non-specific nucleic-acid-binding domain is Sso7d.

Iin another aspect, the invention provides a method of amplifying a subsequence of a target nucleic acid in an aqueous solution using a polymerase chain reaction, the method comprising(i) contacting the target nucleic acid with a protein comprising at least two heterologous domains, wherein a first domain that is a sequence-non-specific nucleic-acid-binding domain is joined to a second domain that is a polymerase domain with error-correcting activity, where the sequence non-specific nucleic-acid-binding domain:(a) binds to double-stranded nucleic acid, and (b) enhances the processivity of the polymerase compared to an identical polymerase not having the sequence non-specific nucleic-acid-binding domain fused to it, and wherein the solution comprises $10^5$ or fewer copies/ml of the target nucleic acid and is of a composition that permits the binding domain to bind to the target nucleic acid and the polymerase domain to extend a primer that is hybridized to the target nucleic acid sequence; (ii) incubating the solution using a polymerase chain reaction temperature profile that amplifies the subsequence. In one embodiment of the method, the nucleic-acid-modifying domain has thermally stable polymerase activity. Often, the nucleic-acid modifying domain comprises a Pyrococcus polymerase domain. In other embodiments of the method, the sequence-non-specific nucleic-acid-binding domain specifically binds to polyclonal antibodies generated against either Sac7d or Sso7d, contains a 50 amino acid subsequence containing 50% amino acid similarity to Sso7D, or specifically binds to polyclonal antibodies generated against Sso7d. In another embodiment, the sequence-non-specific nucleic-acid-binding domain is Sso7d.

Definitions

"Archaeal small basic DNA-binding protein" refers to protein of between 50-75 amino acids having either 50% homology to a natural Archaeal small basic DNA-binding protein such as Sso-7d from *Sulfolobus sulfataricus* or binds to antibodies generated against a native Archaeal small basic DNA-binding protein.

"Catalytic nucleic-acid-modifying domains having a processive nature" refers to a protein sequence or subsequence that performs as an enzyme having the ability to slide along the length of a nucleic acid molecule and chemically alter its structure repeatedly. A catalytic domain can include an entire enzyme, a subsequence thereof, or can include additional amino acid sequences that are not attached to the enzyme or subsequence as found in nature.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Efficiency" in the context of a nucleic acid modifying enzyme of this invention refers to the ability of the enzyme to perform its catalytic function under specific reaction conditions. Typically, "efficiency" as defined herein is indicated by the amount of modified bases generated by the modifying enzyme per binding to a nucleic acid.

"Enhances" in the context of an enzyme refers to improving the activity of the enzyme, i.e., increasing the amount of product per unit enzyme per unit time.

"Fused" refers to linkage by covalent bonding.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Methylase" refers to an enzyme that can modify a nucleic acid by the addition of a methyl group to a nucleotide.

"Nuclease" refers to an enzyme capable of cleaving the phosphodiester bonds between nucleotide subunits of nucleic acids.

"Nucleic-acid-modifying enzyme" refers to an enzyme that covalently alters a nucleic acid.

"Polymerase" refers to an enzyme that performs template-directed synthesis of polynucleotides.

"Error-correcting activity" of a polymerase or polymerase domain refers to the 3' to 5' exonuclease proofreading activity of a template-specific nucleic acid polymerase whereby nucleotides that do not form Watson-Crick base pairs with the template are removed from the 3' end of an oligonucleotide, i.e., a strand being synthesized from a template, in a sequential manner. Examples of polymerases that have error-correcting activity include polymerases from *Pryococcus furiosus, Thermococcus litoralis*, and *Thermotoga maritima.*

"Processivity" refers to the ability of a nucleic acid modifying enzyme to remain attached to the template or substrate and perform multiple modification reactions. Typically "processivity" refers to the ability to modify relatively long tracts of nucleic acid.

"Restriction Endonuclease" refers to any of a group of enzymes, produced by bacteria, that cleave molecules of DNA internally at specific base sequences.

"Sequence-non-specific nucleic-acid-binding domain" refers to a protein domain which binds with significant affinity to a nucleic acid, for which there is no known nucleic acid which binds to the protein domain with more than 100-fold more affinity than another nucleic acid with the same nucleotide composition but a different nucleotide sequence.

"Thermally stable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus, Thermus brockianus*, and *Thermus thermophilus*; any recombinant enzymes deriving from *Thermus* species, and any functional derivatives thereof, whether derived by genetic modification or chemical modification or other methods known in the art.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and *PCR Protocols:A Guide to Methods and Applications*, Innis et al., eds, 1990.

"Long PCR" refers to the amplification of a DNA fragment of 5 kb or longer in length. Long PCR is typically performed using specially-adapted polymerases or polymerase mixtures (see, e.g., U.S. Pat. Nos. 5, 436,149 and 5,512,462) that are distinct from the polymerases conventionally used to amplify shorter products.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-25 nucleotides, in length. The length and sequences of primers for use in PCR can be designed based on principles known to those of skill in the art, see, e.g., Innis et al., supra.

A "temperature profile" refers to the temperature and lengths of time of the denaturation, annealing and/or extension steps of a PCR reaction. A temperature profile for a PCR reaction typically consists of 10 to 60 repetitions of similar or identical shorter temperature profiles; each of these shorter profiles typically define a two step or three-step PCR reaction. Selection of a "temperature profile" is based on various considerations known to those of skill in the art, see, e.g., Innis et al, supra. In a long PCR reaction as described herein, the extension time required to obtain an amplification product of 5 kb or greater in length is reduced compared to conventional polymerase mixtures.

PCR "sensitivity" refers to the ability to amplify a target nucleic acid that is present in low copy number. "Low copy number" refers to $10^5$, often $10^4$, $10^3$, $10^2$, or fewer, copies of the target sequence in the nucleic acid sample to be amplified.

A "template" refers to a double stranded polynucleotide sequence that comprises the polynucleotide to be amplified, flanked by primer hybridization sites. Thus, a "target template" comprises the target polynucleotide sequence flanked by hybridization sites for a 5' primer and a 3' primer.

BRIEF DESCRIPTION OF THE FIGURES

FIGS. 1*a-c* shows the results of PCR amplification reactions performed using primers of different lengths to compare the efficiency of Sso7d-modified polymerase with the unmodifed full-length polymerase.

FIG. 2 shows the results of a PCR amplification reaction using a 12 nt forward primer to evaluate the PCR products generated using Sac7d-ΔTaq compared to Taq.

FIG. 3 shows the results of PCR amplification reactions that demonstrate that Pfu-Sso7d is more efficient than DyNAzyme EXT in long PCR.

DETAILED DESCRIPTION

Introduction

The present invention is the discovery that sequence-non-specific double-stranded nucleic acid binding proteins can be joined to catalytic nucleic acid modifying proteins to enhance the processive nature of the catalytic protein. While the prior art taught that nucleic acid binding proteins can increase the binding affinity of enzymes to nucleic acid, the group of binding proteins having the ability to enhance the processive nature of the enzymes is of particular value. Not to be bound by theory, binding domains of the invention typically dissociate from double-stranded nucleic acid at a very slow rate. Thus, they increase the processivity and/or efficiency of a modifying enzyme to which they are joined by stablizing the enzyme-nucleic acid complex. Accordingly, this invention includes the discovery that DNA-binding domains can stabilize the double-stranded conformation of a nucleic acid and increase the efficiency of a catalytic domain that requires a double-stranded substrate. Described herein are examples and simple assays to readily determine the improvement to the catalytic and/or processive nature of catalytic nucleic acid modifying enzymes.

Catalytic Nucleic-Acid-Modifying Domains.

A catalytic nucleic-acid-modifying domain is the region of a modification enzyme that performs the enzymatic function. The catalytic nucleic-acid modifying domains of the invention can be processive, e.g., polymerase, exonuclease, etc., or non-processive, e.g., ligases, restriction endonucleases, etc.

Processivity reflects the ability of a nucleic acid modifying enzyme to synthesize or perform multiple modifications, e.g., nucleotide additions or methylations, in a single binding event. The processive proteins of the present invention exhibit enhanced processivity due to the presence of a sequence-non-specific double-stranded DNA binding domain that is joined to the processive modifying enzyme (or the enzymatic domain of the modifying enzyme), thereby providing a tethering domain to stabilize the nucleic acid/enzyme complex. Often the binding domain is from a thermostable organism and provides enhanced activity at higher temperatures, e.g., temperatures above 45° C. Examples of processive modifying enzymes include DNA polymerases, RNA polymerases, reverse transcriptases, methylases, 3' or 5' exonucleases, gyrases, and topoisomerase.

Polymerases

DNA polymerases are well-known to those skilled in the art. These include both DNA-dependent polymerases and RNA-dependent polymerases such as reverse transcriptase. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases $\alpha$,$\delta$, and $\epsilon$, are implicated in nuclear replication, and a family A polymerase, polymerase $\gamma$, is used for mitochondrial DNA replication. Other types of DNA polymerases include phage polymerases.

Similarly, RNA polymerase typically include eukaryotic RNA polymerases I, II, and III, and bacterial RNA polymerases as well as phage and viral polymerases. RNA polymerases can be DNA-dependent and RNA-dependent.

In one embodiment, polymerase domains that have an error-correcting activity are used as the catalytic domain of the improved polymerases described herein. These polymerases can be used to obtain long, i.e., 5 kb, often 10 kb, or greater in length, PCR products. "Long PCR" using these improved polymerases can be performed using extension times that are reduced compared to prior art "long PCR" polymerase and/or polymerase mixtures. Extension times of less than 30 seconds per kb, often 15 seconds per kb, can be used to amplify long products in PCR reactions using the improved polymerases. Furthermore, these modified polymerases also exhibit increased sensitivity.

Prior-art non-error-correcting polymerases such as Taq polymerase are capable of amplifying DNA from very small input copy concentrations, such as, in the extreme, 10 copies per ml. However, because of the low fidelity of such polymerases, products cloned from such amplifications are likely to contain introduced mutations.

Prior-art error-correcting polymerases such as Pfu copy DNA with higher fidelity than Taq, but are not capable of amplifying DNA from small input copy concentrations. The most likely explanation for such failure is the very low processivity of these enzymes. The hybrid error-correcting polymerases of the invention exhibit much higher processivity while retaining error-correcting activity and thereby provide both sensitivity and fidelity in amplification reactions.

Other Modifying Enzymes

Typically, DNA gyrases and topoisomerases play a role in higher orders of DNA structures such as supercoiling. DNA gyrases introduce negative supercoils. In prokaryotes, the A subunit is responsible for DNA cutting and reunion and the B subunit contains the ATP-hydrolysis activity. DNA gyrase introduces supercoiling processively and catalytically, typically introducing up to 100 supercoils per minute per molecule of DNA gyrase. In the absence of ATP, gyrase will slowly relax negative supercoils.

Topoisomerases are enzymes found in both prokaryotes and eukaryotes that catalyze the interconversion of different topological isomers of DNA, thereby causing a change in the link number. Topoisomerases can remove negative or positive supercoils from DNA or can introduce negative supercoils.

A variety of methylases and 3' or 5' exonucleases are also described in the art including bacterial, prokaryotic, eukaryotic and phage enzymes. Typically, exonucleases, such as lambda exonuclease, and some methylases are also processive.

The activity of a catalytic subunit can be measured using assays well known to those of skill in the art. For example, a processive enzymatic activity, such as a polymerase activity, can be measured by determining the amount of nucleic acid synthesized in a reaction, such as a polymerase chain reaction. In determining the relative efficiency of the enzyme, the amount of product obtained with a modifying enzyme of the invention, e.g. a polymerase containing a sequence-non-specific double-stranded DNA binding domain, can then be compared to the amount of product obtained with the normal modifying enzyme, which will be described in more detail below and in the Examples.

Modifying enzymes such as ligases or restriction endonucleases bind to double-stranded nucleic acids to perform the modifying function. The catalytic activity is typically measured by determining the amount of modified product produced under particular assay conditions. For example, ligase activity can be assayed by determining the amount of circularized plasmid, which had previously been digested with a restriction endonuclease to generate compatible ends, in a ligation reaction following incubation by quantifying the number of transformants obtained with an aliquot of the ligation reaction. Activity of a restriction endonuclease can be determined by assaying the extent of digestion of the target DNA, for example, by analyzing the extent of digestion of the DNA on a gel.

A catalytic modifying domain suitable for use in the invention can be the modifying enzyme itself or the catalytic modifying domain, e.g., Taq polymerase or a domain of Taq with polymerase activity. The catalytic domain may include additional amino acids and/or may be a variant that contains amino acid substitutions, deletions or additions, but still retains enzymatic activity.

Sequence-Non-Specific Nucleic-Acid-Binding Domain.

A double-stranded sequence-non-specific nucleic acid binding domain is a protein or defined region of a protein that binds to double-stranded nucleic acid in a sequence-independent manner, i.e., binding does not exhibit a gross preference for a particular sequence. Typically, double-stranded nucleic acid binding proteins exhibit a 10-fold or higher affinity for double-stranded versus single-stranded nucleic acids. The double-stranded nucleic acid binding proteins in particular embodiments of the invention are preferably thennostable. Examples of such proteins include, but are not limited to, the Archaeal small basic DNA binding proteins Sac7d and Sso7d (see, e.g., Choli et al., *Biochimica et Biophysica Acta* 950: 193-203, 1988; Baumann et al., *Structural Biol.* 1:808-819, 1994; and Gao et al, *Nature Struc. Biol.* 5:782-786, 1998), Archael HMf-like proteins (see, e.g., Starich et al., *J Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell*:99, 155-166, 1999; De Felice et al., *J. Molec. Biol.* 291, 47-57, 1999; and Zhang et al., *Biochemistry* 34:10703-10712, 1995).

Sso7d and Sac 7d

Sso7d and Sac7d are small (about 7,000 kd MW), basic chromosomal proteins from the hyperthermophilic archaeabacteria *Sulfolobus solfataricus* and *S. acidocaldarius*, respectively. These proteins are lysine-rich and have high thermal, acid and chemical stability. They bind DNA in a sequence-independent manner and when bound, increase the $T_M$ of DNA by up to 40° C. under some conditions (McAfee et al., *Biochemistry* 34:10063-10077, 1995). These proteins and their homologs are typically believed to be involved in stabilizing genomic DNA at elevated temperatures.

HMF-like Proteins

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to Taq DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

PCNA Homologs

Many but not all family B DNA polymerases interact with accessory proteins to achieve highly processive DNA synthesis. A particularly important class of accessory proteins is referred to as the sliding clamp. Several characterized sliding clamps exist as trimers in solution, and can form a ring-like structure with a central passage capable of accommodating double-stranded DNA. The sliding clamp forms specific interactions with the amino acids located at the C terminus of particular DNA polymerases, and tethers those polymerases to the DNA template during replication. The sliding clamp in eukarya is referred to as the proliferating cell nuclear antigen (PCNA), while similar proteins in other domains are often referred to as PCNA homologs. These homologs have marked structural similarity but limited sequence similarity.

Recently, PCNA homologs have been identified from thermophilic Archaea (e.g., *Sulfalobus sofataricus, Pyroccocus furiosus*, etc.). Some family B polymerases in Archaea have a C terminus containing a consensus PCNA-interacting amino acid sequence and are capable of using a PCNA homolog as a processivity factor (see, e.g., Cann et al., *J. Bacteriol.* 181: 6591-6599, 1999 and De Felice et al., *J Mol. Biol.* 291:47-57, 1999). These PCNA homologs are useful sequence-non-specific double-stranded DNA binding domains for the invention. For example, a consensus PCNA-interacting sequence can be joined to a polymerase that does not naturally interact with a PCNA homolog, thereby allowing a PCNA homolog to serve as a processivity factor for the polymerase. By way of illustration, the PCNA-interacting sequence from *Pyrococcus furiosus* PolII (a heterodimeric DNA polymerase containing two family B-like polypeptides) can be covalently joined to *Pyrococcus furiosus* PolI (a monomeric family B polymerase that does not normally interact with a PCNA homolog). The resulting fusion protein can then be allowed to associate non-covalently with the *Pyrococcus furiosus* PCNA homolog to generate a novel heterologous protein with increased processivity relative to the unmodified *Pyrococcus furiosus* PolI.

Other Sequence-nonspecific Double-stranded Nucleic Acid Binding Domains

Additional nucleic acid binding domains suitable for use in the invention can be identified by homology with known sequence non-specific double-stranded DNA binding proteins and/or by antibody crossreactivity, or may be found by means of a biochemical assay.

Identification of Nucleic Acid Binding Domains Based on Homology.

Typically, domains that have about 50% amino acid sequence identity, optionally about 60%, 75, 80, 85, 90, or 95-98% amino acid sequence identity to a known sequence non-specific double-stranded nucleic acid binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the following sequence comparison algorithms or by manual alignment and visual inspection. For purposes of this patent, percent amino acid identity is determined by the default parameters of BLAST.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The comparison window includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One example of a useful algorithm is PILEUP. PILEUP creates a multiple sequence alignment from a group of related sequences using progressive, pair-wise alignments to show relationship and percent sequence identity. It also plots a tree or dendogram showing the clustering relationships used to create the alignment. PILEUP uses a simplification of the progressive alignment method of Feng & Doolittle, J. Mol. Evol. 35:351-360 (1987). The method used is similar to the method described by Higgins & Sharp, CABIOS 5:151-153 (1989). The program can align up to 300 sequences, each of a maximum length of 5,000 nucleotides or amino acids. The multiple alignment procedure begins with the pair-wise alignment of the two most similar sequences, producing a cluster of two aligned sequences. This cluster is then aligned to the next most related sequence or cluster of aligned sequences. Two clusters of sequences are aligned by a simple extension of the pair-wise alignment of two individual sequences. The final alignment is achieved by a series of progressive, pair-wise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters:default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when:the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci.* USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci.* USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Cross-reactive Binding to Antibodies

Sequence non-specific doubled-stranded nucleic acid binding domains for use in the invention can also be identified by cross-reactivity using antibodies, preferably polyclonal antibodies, that bind to known nucleic acid binding domains. Polyclonal antibodies are generated using methods well known to those of ordinary skill in the art (see, e.g., Coligan, *Current Protocols in Immunology* (1991); Harlow & Lane, *Antibodies, A Laboratory Manual* (1988)). Those proteins that are immunologically cross-reactive binding proteins can then be detected by a variety of assay methods. For descriptions of various formats and conditions that can be used, see, e.g., *Methods in Cell Biology:Antibodies in Cell Biology*, volume 37 (Asai, ed. 1993), Coligan, supra, and Harlow & Lane, supra.

Useful immunoassay formats include assays where a sample protein is immobilized to a solid support. For example, a cross-reactive binding protein can be identified using an immunoblot analysis such as a western blot. The western blot technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that bind to the sequence non-specific double-stranded nucleic acid binding domain. The antibodies specifically bind to cross-reactive polypeptides on the solid support. The antibodies may be directly labeled or alternatively may be subsequently detected using labeled antibodies (e.g., labeled sheep anti-mouse antibodies) that specifically bind to the anti-binding domain antibodies. Other immunoblot assays, such as analysis of recombinant protein libraries, are also useful for identifying proteins suitable for use in the invention.

Using this methodology under designated immunoassay conditions, immunologically cross-reactive proteins that bind to a particular antibody at least two times the background or more, typically more than 10 times background, and do not substantially bind in a significant amount to other proteins present in the sample can be identified.

Immunoassays in the competitive binding format can also be used for crossreactivity determinations. For example, polyclonal antisera are generated to a known, sequence non-specific double-stranded nucleic acid binding domain protein, e.g., a *Pyrococcus furiosus* (Pfu) PCNA. The target antigen can then be immobilized to a solid support. Non-target antigens having minor crossreactivity (if they exist) can be added to the assay to improve the selectivity of the sera. The ability of the added proteins to compete for binding of the antisera to the immobilized protein is compared to the ability of the binding domain protein, in this example Pfu PCNA, to compete with itself. The percent crossreactivity for the above proteins is calculated, using standard calculations. Those antisera with less than 10% crossreactivity with the added protein are selected and pooled. Cross-reacting antibodies to non-target antigens can also be removed from the pooled antisera by immunoabsorption with the non-target antigens. Antibodies that specifically bind to particular nucleic acid binding domains of the invention can also be made using this methodology.

The immunoabsorbed and pooled antisera are then used in a competitive binding immunoassay as described above to compare a second protein, thought to be perhaps an allele, polymorphic variant or a homolog of the known binding domain, for example, a PCNA homolog from another *Pyrococcus* sp., to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the nucleic acid binding domain protein that is required to inhibit 50% of binding, then the second protein is said to specifically bind to the polyclonal antibodies generated to the nucleic acid binding domain immunogen.

Assays for Sequence Non-specific Double-stranded Nucleic Acid Binding Activity

The activity of the sequence non-specific double-stranded nucleic acid binding domains can be assessed using a variety of assays. Suitable binding domains exhibit a marked preference for double-stranded vs. single-stranded nucleic acids.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radio-labeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain suitable for use in the invention binds to double-stranded nucleic acids in a sequence-independent fashion, i.e., a binding domain of the invention binds double-stranded nucleic acids with a significant affinity, but, there is no known nucleic acid that binds to the domain with more than 100-fold more affinity than another nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific double-stranded nucleic acid binding domains for use in the invention can also be assessed, for example, by assaying the ability of the double-stranded binding domain to increase processivity or efficiency of a modifying enzyme or to increase the stability of a nucleic acid duplex by at least 1° C. can be determined. These techniques are discussed below in the section describing the analysis for enhanced efficiency of a nucleic acid modifying enzyme.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_M$ of the double-stranded substrate can be determined from the midpoint of the melting curve. The effect of the sequence-non-specific double-stranded nucleic-acid-binding protein on the $T_M$ can then be determined by comparing the $T_M$ obtained in the presence of the modified enzyme with that in the presence of the unmodified enzyme. (The protein does not significantly contribute to the UV absorbance because it has a much lower extinction coefficient at 260 nm than DNA). A domain that increases the $T_M$ by 1°, often by 5°, 10° or more, can then be selected for use in the invention.

Novel sequence non-specific double-stranded nucleic acid binding proteins of the invention can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

Joining the Catalytic Domain with the Nucleic-Acid-Binding Domain.

The catalytic domain and the double-stranded nucleic-acid-binding domain can be joined by methods well known to those of skill in the art. These methods include chemical and recombinant means.

Chemical means of joining the heterologous domains are described, e.g., in *Bioconjugate Techniques*, Hermanson, Ed., Academic Press (1996). These include, for example, derivitization for the purpose of linking the moieties to each other, either directly or through a linking compound, by methods that are well known in the art of protein chemistry. For example, in one chemical conjugation embodiment, the means of linking the catalytic domain and the nucleic acid binding domain comprises a heterobifunctional coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

The means of linking the heterologous domains of the protein may also comprise a peptidyl bond formed between moieties that are separately synthesized by standard peptide synthesis chemistry or recombinant means. The protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) *J Am. Chem. Soc.*, 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, *Proteins Structures and Molecular Principles*, 50-60 (1983)). The composition of the synthetic polypeptides or of subfragments of the polypeptide, may be confirmed by amino acid analysis or sequencing (e.g., the Edman degradation procedure; see Creighton, *Proteins, Structures and Molecular Principles*, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In another embodiment, the domains of a protein of the invention, e.g., Sso7d and Taq polymerase, are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

In a specific embodiment, the coding sequences of each polypeptide in the fusion protein are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors:(1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Val and Thr residues. Other near neutral amino acids, such as Ser and Ala can also be used in the linker sequence. Amino acid sequences which may be usefully employed as linkers include those disclosed in Maratea et al. (1985) Gene 40:39-46; Murphy et al. (1986) *Proc. Natl. Acad. Sci. USA* 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterofunctional linkages.

Other methods ofjoining the domains include ionic binding by expressing negative and positive tails and indirect binding through antibodies and streptavidin-biotin interactions. (See, e.g., *Bioconjugate Techniques*, supra). The domains may also be joined together through an intermediate interacting sequence. For example, a consensus PCNA-interacting sequence can be joined to a polymerase that does not naturally interact with a PCNA homolog. The resulting fusion protein can then be allowed to associate non-covalently with the PCNA homolog to generate a novel heterologous protein with increased processivity.

Production of Fusion Proteins using Recombinant Techniques

In one embodiment, a protein of the invention is produced by recombinant expression of a nucleic acid encoding the protein, which is well known to those of skill in the art. Such a fusion product can be made by ligating the appropriate nucleic acid sequences encoding the desired amino acid sequences to each other by methods known in the art, in the proper coding frame, and expressing the product by methods known in the art.

Nucleic acids encoding the domains to be incorporated into the fusion proteins of the invention can be obtained using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression:A Laboratory Manual* (1990); and *Current Protocols in Molecular Biology* (Ausubel et al., eds., 1994)).

Often, the nucleic acid sequences encoding catalytic or nucleic acid binding domains or related nucleic acid sequence homologs are cloned from cDNA and genomic DNA libraries by hybridization with probes, or isolated using amplification techniques with oligonucleotide primers. Amplification techniques can be used to amplify and isolate sequences from DNA or RNA (see, e.g., Dieffenfach & Dveksler, PCR Primers:A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes.

In an example of obtaining a nucleic acid encoding a catalytic or nucleic acid binding domain using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; PCR *Protocols A Guide to Methods and Applications* (Innis et al., eds) Academic Press Inc. San Diego, Calif. (1990) (Innis); Arnheim & Levinson (Oct. 1, 1990) C&EN 36-47*; The Journal Of NIH Research* (1991) 3:81-94; (Kwoh et al (1989) *Proc. Natl. Acad. Sci. USA* 86:1173; Guatelli et al. (1990) *Proc. Natl. Acad. Sci. USA* 87, 1874; Lomell et al (1989) *J Clin. Chem*., 35:1826; Landegren et al., (1988) *Science* 241:1077-1080; Van Brunt (1990) *Bio-*

*technology* 8:291-294; Wu and Wallace (1989) *Gene* 4:560; and Barringer et al. (1990) *Gene* 89:117.

Other physical properties of a polypeptide expressed from a particular nucleic acid can be compared to properties of known sequence nonspecific double-stranded nucleic acid binding proteins or nucleic acid modifying enzyme catalytic domains to provide another method of identifying suitable nucleic acids.

In some embodiments, it may be desirable to modify the polypeptides encoding the catalytic and/or nucleic acid binding regions of the recombinant fusion protein. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328:731-734.

For example, the catalytic and/or nucleic acid binding domains can be modified to facilitate the linkage of the two domains to obtain the polynucleotides that encode the fusion polypeptides of the invention. Catalytic domains and binding domains that are modified by such methods are also part of the invention. For example, a codon for a cysteine residue can be placed at either end of a domain so that the domain can be linked by, for example, a sulfide linkage. The modification can be performed using either recombinant or chemical methods (see, e.g., Pierce Chemical Co. catalog, Rockford Ill.).

The catalytic and binding domains of the recombinant fusion protein are often joined by linker domains, usually polypeptide sequences such as those described above, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In some embodiments, the recombinant nucleic acids the recombinant nucleic acids encoding the proteins of the invention are modified to provide preferred codons which enhance translation of the nucleic acid in a selected organism (e.g., yeast preferred codons are substituted into a coding nucleic acid for expression in yeast).

Expression Cassettes and Host Cells for Expressing the Fusion Polypeptides

There are many expression systems for producing the fusion polypeptide that are well know to those of ordinary skill in the art. (See, e.g., *Gene Expression Systems*, Fernandex and Hoeffler, Eds. Academic Press, 1999.) Typically, the polynucleotide that encodes the fusion polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the nucleic acids that encode the joined polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198:1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., pBLUESCRIPT™, pSKF, pET23D, λ-phage derived vectors, and fusion expression systems such as GST and LacZ. Epitope tags can also be added to recombinant proteins to provide convenient methods of isolation, e.g., c-myc, HA-tag, 6-His (SEQ ID NO:30) tag, maltose binding protein, VSV-G tag, anti-DYKDDDDK (SEQ ID NO:31) tag, or any such tag, a large number of which are well known to those of skill in the art.

For expression of fusion polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in Bacillus in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25:167; de Boer et al. (1983) *Proc. Nat'l. Acad. Sci. USA* 80:21), and the bacteriophage T7 promoter (Studier et al. (1986) *J Mol Biol*.; Tabor et al. (1985) *Proc. Nat'l. Acad. Sci. USA* 82:1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J Biol. Chem.* 263: 16297-16302.

The construction of polynucleotide constructs generally requires the use of vectors able to replicate in bacteria. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3:151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology* Vol. 182: *Guide to Protein Purification*., Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering:Principles and Methods, J. K. Setlow, Ed., Plenum Press, NY; commercially available from Qiagen (Santa Clarita, Calif.)).

One of skill would recognize that modifications could be made to the catalytic and sequence nonspecific double-stranded nucleic acid binding domains without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

Assays to Determine Improved Activity for the Catalytic Domains.

Activity of the catalytic domain can be measured using a variety of assays that can be used to compare processivity or modification activity of a modifying protein domain joined to a binding domain compared to the protein by itself. Improvement in activity includes both increased processivity and increased efficiency.

Improved Activity of Processive Modifying Enzymes

Polymerase processivity can be measured in variety of methods known to those of ordinary skill in the art. Polymerase processivity is generally defined as the number of nucleotides incorporated during a single binding event of a modifying enzyme to a primed template.

For example, a 5' FAM-labeled primer is annealed to circular or linearized ssM 13mp 18 DNA to form a primed template. In measuring processivity, the primed template usually is present in significant molar excess to the enzyme or catalytic domain to be assayed so that the chance of any primed template being extended more than once by the polymerase is minimized. The primed template is therefore mixed with the polymerase catalytic domain to be assayed at a ratio such as approximately 4000:1 (primed DNA:DNA polymerase) in the presence of buffer and dNTPs. $MgCl_2$ is added to initiate DNA synthesis. Samples are quenched at various times after initiation, and analyzed on a sequencing gel. At a polymerase concentration where the median product length does not change with time or polymerase concentration, the length corresponds to the processivity of the enzyme. The processivity of a protein of the invention, i.e., a protein that contains a sequence non-specific double-stranded nucleic acid binding domain fused to the catalytic domain of a processive nucleic acid modifying enzyme such as a polymerase, is then compared to the processivity of the enzyme without the binding domain.

Enhanced efficiency can also be demonstrated by measuring the increased ability of an enzyme to produce product. Such an analysis measures the stability of the double-stranded nucleic acid duplex indirectly by determining the amount of product obtained in a reaction. For example, a PCR assay can be used to measure the amount of PCR product obtained with a short, e.g., 12 nucleotide in length, primer annealed at an elevated temperature, e.g., 50° C. In this analysis, enhanced efficiency is shown by the ability of a polymerase such as a Taq polymerase to produce more product in a PCR reaction using the 12 nucleotide primer annealed at 50° C. when it is joined to a sequence-non-specific double-stranded nucleic-acid-binding domain of the invention, e.g., Sso7d, than Taq polymerase does alone. In contrast, a binding tract that is a series of charged residues, e.g. lysines, when joined to a polymerase does not enhance processivity.

Similar assay conditions can be employed to test for improved processivity when the catalytic domain is a reverse transcriptase, methylase, gyrase, topoisomerase, or an exonuclease. In these analyses, processivity is measured as the ability of the enzyme to remain attached to the template or substrate and perform multiple modification reactions. The molar ratio of nucleic acid to enzyme is typically sufficiently high so that one the average only one enzyme molecule is bound per substrate nucleic acid. For example, the activity of a processive exonuclease, lambda exonuclease, can be assayed using published methods (see, e.g., Mitsis and Kwagh, *Nucleic Acid Research*, 27:3057-3063, 1999). In brief, a long DNA substrates (0.5-20 kb) can be amplified from a DNA template using a 5'-biotinylated primer as the forward primer and a 5' phosphorylated primer as the reverse primer, or vice versa. Radio-labeled dATP is used to internally label the PCR fragment, which serves as the substrate for the lambda exonuclease. The purified internally-labeled substrate is mixed with the enzyme at a sufficient high molar ratio of DNA to enzyme to ensure that on average only one exonuclease molecule bound per substrate DNA. Aliquots of the sample are removed over time and can be assayed either by gel electrophoresis or by monitoring the formation of acid soluble radio-labels.

Enhanced Activity of Non-processive Modifying Enzymes

Catalytic domains of non-processive DNA modifying enzymes, or the enzymes themselves, can also be used in the invention. Examples of such modifying enzymes include ligases and restriction endonucleases. Often, the catalytic domains are obtained from thermostable *Thermus* or *Pyrococcus* species. To determine improved activity, the enzymatic function can be analyzed under a variety of conditions, often increased reaction temperatures, e.g., temperatures 45° C. or above, and compared to the unmodified enzyme activity.

For example, Taq DNA ligase catalyzes the formation of a phosphodiester bond between juxtaposed 5' phosphate and 3' hydroxyl termini of two adjacent oligonucleotides that are hybridized to a complementary target DNA. The enzyme is active at 45° C.-65° C. The yield of the ligated product is dependent on how efficiently the complementary strands of DNA are annealed to form the substrate for the enzyme. A binding domain of the invention, such as a Sso7d-like protein, when joined to the ligase can stabilize the DNA duplex by increasing its melting temperature, so that an elevated reaction temperature can be used to maximize the activity of the enzyme without compromising the basepairing interactions.

The effect of Sso7d fusion on the activity of a ligase can be analyzed by comparing the ligation efficiency of the modified versus that of the unmodified enzyme. The ligation efficiency of two linear DNA fragments can be monitored by agarose gel electrophoresis, whereas the ligation efficiency of converting a linearized plasmid to a circular plasmid can be monitored by DNA transformation.

In another example, the catalytic domain of a nucleic acid modifying enzyme with improved activity can be from a restriction enzyme isolated from a thermophilic species that requires an elevated reaction temperature to achieve optimal activity. For example when the restriction enzyme recognition sites are located very close to the end of a DNA fragment or in duplexed oligonucleotides, higher temperatures may destabilize the duplex structure. At a higher reaction temperature, e.g., 45° C. or above, a restriction enzyme with improved activity because of the presence of a binding domain of the invention, e.g., an Sso7d-like protein joined to the restriction endonuclease, can produce a greater amount of product, i.e., digested DNA, than the restriction enzyme by itself. The product yield from a particular reaction can be assessed by visualization on a gel or by assessment of transformation efficiency.

Other methods of assessing enhanced efficiency of the improved nucleic acid modifying enzymes of the invention can be determined by those of ordinary skill in the art using standard assays of the enzymatic activity of a given modification enzyme. Thus, processive modifying enzymes such as reverse transcriptases, methylases, gyrases, and topoisomerases, and other non-processive modifying enzymes can be similarly analyzed by comparing activities of the protein, or a catalytic domain, joined to a sequence non-specific double-stranded nucleic acid binding domain and the protein by itself.

All publications, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of non-critical parameters that could be changed or modified to yield essentially similar results.

Example 1

Construction of Fusion Proteins

Construction of Sso 7d-ΔTaq fusion.

The following example illustrates the construction of a polymerase protein possessing enhanced processivity, in which the sequence-non-specific double-stranded nucleic acid binding protein Sso7d is fused to the *Thermus aquaticus* PolI DNA polymerase (a family A polymerase known as Taq DNA polymerase) that is deleted at the N terminus by 289 amino acids (ΔTaq).

Based on the published amino acid sequence of Sso7d, seven oligonucleotides were used in constructing a synthetic gene encoding Sso7d. The oligonucleotides were annealed and ligated using T4 DNA ligase. The final ligated product was used as the template in a PCR reaction using two terminal oligonucleotides as primers to amplify the full-length gene. By design, the resulting PCR fragment contains a unique EcoRI site at the 5' terminus, and a unique BstXI site at the 3' terminus. In addition to encoding the Sso7d protein, the above PCR fragment also encodes a peptide linker with the amino acid sequence of Gly-Gly-Val-Thr (SEQ ID NO:32) positioned at the C terminus of the Sso7d protein. The synthetic gene of Sso7d has the DNA sequence shown in SEQ ID NO: 1, and it encodes a polypeptide with the amino acid sequence shown in SEQ ID NO:2.

The synthetic gene encoding Sso7d was then used to generate a fusion protein in which Sso7d replaces the first 289 amino acid of Taq. The fragment encoding Sso7d was subcloned into a plasmid encoding Taq polymerase to generate the fusion protein, as follows. Briefly, the DNA fragment containing the synthetic Sso7d gene was digested with restriction endonucleases EcoRI and BstXI, and ligated into the corresponding sites of a plasmid encoding Taq. As the result, the region that encodes the first 289 amino acid of Taq is replaced by the synthetic gene of Sso7d. This plasmid (pYW1) allows the expression of a single polypeptide containing Sso7d fused to the N terminus of ΔTaq via a synthetic linker composed of Gly-Gly-Val-Thr (SEQ ID NO:32). The DNA sequence encoding the fusion protein (Sso7d-ΔTaq) and the amino acid sequence of the protein are shown in SEQ ID NOs:3 and 4, respectively.

Construction of Sso 7d-Taq Fusion.

An Sso7d/full-length Taq fusion protein was also constructed. Briefly, a 1 kb PCR fragment encoding the first 336 amino acids of Taq polymerase was generated using two primers. The 5' primer introduces a SpeI site into the 5' terminus of the PCR fragment, and the 3' primer hybridizes to nucleotides 1008-1026 of the Taq gene. The fragment was digested with SpeI and BstXI, releasing a 0.9 kb fragment encoding the first 289 amino acids of Taq polymerase. The 0.9 kb fragment was ligated into plasmid pYW1 at the SpeI (located in the region encoding the linker) and BstXI sites. The resulting plasmid (pYW2) allows the expression of a single polypeptide containing the Sso7d protein fused to the N terminus of the full length Taq DNA polymerase via a linker composed of Gly-Gly-Val-Thr (SEQ ID NO:32), the same as in Sso7d-ΔTaq. The DNA sequence encoding the Sso7d-Taq fusion protein and the amino acid sequence of the protein are shown in SEG ID NOs:5 and 6, respectively.

Construction of Pfu-Sso 7d Fusion.

A third fusion protein was created, joining Sso7d to the C terminus of *Pyrococcus furiosus* DNA poll (a family B DNA polymerase known as Pfu). A pET-based plasmid carrying the Pfu DNA polymerase gene was modified so that a unique KpnI site and a unique SpeI site are introduced at the 3' end of the Pfu gene before the stop codon. The resulting plasmid (pPFKS) expresses a Pfu polymerase with three additional amino acids (Gly-Thr-His) at its C terminus.

Two primers were used to PCR amplify the synthetic Sso7d gene described above to introduce a Kpn I site and a NheI site flanking the Sso7d gene. The 5' primer also introduced six additional amino acids (Gly-Thr-Gly-Gly-Gly-Gly: SEQ ID NO:33), which serve as a linker, at the N terminus of the Sso7d protein. Upon digestion with KpnI and NheI, the PCR fragment was ligated into pPFKS at the corresponding sites. The resulting plasmid (pPFS) allows the expression of a single polypeptide containing Sso7d protein fused to the C terminus of the Pfu polyrnerase via a peptide linker (Gly-Thr-Gly-Gly-Gly-Gly: SEQ ID NO:33). The DNA sequence encoding the fusion protein (Pfu-Sso7d) and the amino acid sequence of the fusion protein are shown in SEQ ID NOs: 7 and 8, respectively.

Construction of Sac7d-ΔTaq Fusion.

A fourth fusion protein was constructed, which joined a sequence-non-specific DNA binding protein from a different species to ΔTaq. Two primers were used to PCR amplify the Sac7d gene from genomic DNA of *Sulfolobus acidocaldarius*. The primers introduced a unique EcoRI site and a unique SpeI site to the PCR fragment at the 5' and 3' termini, respectively. Upon restriction digestion with EcoRI and SpeI, the PCR fragment was ligated into pYW1 (described above) at the corresponding sites. The resulting plasmid expresses a single polypeptide containing the Sac7d protein fused to the N terminus of ΔTaq via the same linker as used in Sso7d-ΔTaq. The DNA sequence of the fusion protein (Sac7d-ΔTaq) and the amino acid sequence of the protein are shown in SEQ ID. NOs:9 and 10, respectively.

Construction of PL-ΔTaq Fusion.

A fifth fusion protein joins a peptide composed of 14 lysines and 2 arginines to the N terminus of ΔTaq. To generate the polylysine (PL)-ΔTaq fusion protein, two 67 nt oligonucleotides were annealed to form a duplexed DNA fragment with a 5' protruding end compatible with an EcoRI site, and a 3' protruding end compatible with an SpeI site. The DNA fragment encodes a lysine-rich peptide of the following composition: NSKKKKKKKRKKRKKKGGGVT (SEQ ID NO:34). The numbers of lysines and arginines in this peptide are identical to the that in Sso7d. This DNA fragment was ligated into pYW1, predigested with EcoRI and SpeI, to replace the region encoding Sso7d. The resulting plasmid (pLST) expresses a single polypeptide containing the lysine-rich peptide fused to the N terminus of ΔTaq. The DNA sequence encoding the fusion protein (PL-ΔTaq) and the amino acid sequence of the protein are shown in SEQ ID NOs:11 and 12, respectively.

Example 2

Assessing the Processivity of the Fusion Polymerases

This example illustrates enhancement of processivity of the fusion proteins of the invention generated in Example 1.

Polymerase Unit Definition Assay

The following assay was used to define a polymerase unit. An oligonucleotide was pre-annealed to ssM13 mp 18 DNA in the presence of $Mg^{++}$-free reaction buffer and dNTPs. The DNA polymerase of interest was added to the primed DNA mixture. $MgCl_2$ was added to initiate DNA synthesis at 72° C. Samples were taken at various time points and added to TE buffer containing PicoGreen (Molecular Probes, Eugene Oreg.). The amount of DNA synthesized was quantified using a fluorescence plate reader. The unit activity of the DNA polymerase of interest was determined by comparing its initial rate with that of a control DNA polymerase (e.g., a commercial polymerase of known unit concentration).

Processivity Assay

Processivity was measured by determining the number of nucleotides incorporated during a single binding event of the polymerase to a primed template.

Briefly, 40 nM of a 5' FAM-labeled primer (34 nt long) was annealed to 80 nM of circular or linearized ssM13 mp18 DNA to form the primed template. The primed template was mixed with the DNA polymerase of interest at a molar ratio of approximately 4000:1 (primed DNA:DNA polymerase) in the presence of standard PCR buffer (free of $Mg^{++}$)and 200 μM of each dNTPs. $MgCl_2$ was added to a final concentration of 2 mM to initiate DNA synthesis. At various times after initiation, samples were quenched with sequencing loading dye containing 99% formamide, and analyzed on a sequencing gel. The median product length, which is defined as the product length above or below which there are equal amounts of products, was determined based on integration of all detectable product peaks. At a polymerase concentration for which the median product length change with time or polymerase concentration, the length corresponds to the processivity of the enzyme. The ranges presented in Table 1 represent the range of values obtained in several repeats of the assay.

TABLE I

Comparison of processivity

| DNA polymerase | Median product length (nt) |
|---|---|
| ΔTaq | 2-6 |
| Sso7d-ΔTaq | 39-58 |
| PL-ΔTaq | 2-6 |
| Taq | 15-20 |
| Sso7d-Taq | 130-160 |
| Pfu | 2-3 |
| Pfu-Sso7d | 35-39 |

In comparing the processivity of modified enzyme to the unmodified enzyme, ΔTaq had a processivity of 2-6 nucleotides, whereas Sso7d-ΔTaq fusion exhibited a processivity of 39-58 nucleotides (Table I). Full length Taq had a processivity of 15-20 nucleotides, which was significantly lower than that of Sso7d-Taq fusion with a processivity of 130-160 nucleotides. These results demonstrate that Sso7d joined to Taq polymerase enhanced the processivity of the polymerase.

Pfu belongs to family B of polymerases. Unlike Taq polymerase, Pfu possesses a 3' to 5' exonuclease activity, allowing it to maintain high fidelity during DNA synthesis. A modified Pfu polymerase, in which Sso7d is fused to the C terminus of the full length Pfu polymerase, and an unmodified Pfu polymerase were analyzed in the processivity assay described above. As shown in Table I, the Pfu polymerase exhibited a processivity of 2-3 nt, whereas the Pfu-Sso7d fusion protein had a processivity of 35-39 nt. Thus, the fusion of Sso7d to the C terminus of Pfu resulted in a >10-fold enhancement of the processivity over the unmodified enzyme.

The ability of a lysine-rich peptide to enhance the processivity of Taq polymerase was also assessed. The processivity of PL-ΔTaq was measured using the method described above, and compared to that of the unmodified protein, ΔTaq. As shown in Table I, the presence of the polylysine tract did not enhance the processivity of ΔTaq. Thus, although the addition of a lysine-rich peptide to a nucleic acid binding protein may increase the association rate of an enzyme to its substrate as disclosed in the prior art, processivity is not increased.

Example 3

Effect of Fusion Proteins on Oligonucleotide Annealing Temperature

This experiment demonstrates the increased efficiency of the Sso7d-ΔTaq fusion protein, compared to Taq, to produce product at higher annealing temperatures by stabilizing dsDNA.

Two primers, primer 1008 (19mer; $T_M$=56.4° C.) and 2180R (20mer; $T_M$=56.9° C.), were used to amplify a 1 kb fragment (1008-2180) of the Taq pol gene. A gradient thermal cycler (M J Research, Waltham Mass.) was used to vary the annealing temperature from 50° C. to 72° C. in a PCR cycling program. The amounts of PCR products generated using identical number of units of Sso7d-ΔTaq and Taq were quantified and compared. The results are shown in Table II. The Sso7d-ΔTaq fusion protein exhibited significantly higher efficiency than full length Taq at higher annealing temperatures. Thus, the presence of Sso7d in cis increases the melting temperature of the primer on the template.

The annealing temperature assay above was used to investigate whether PL-ΔTaq has any effect on the annealing temperature of primer during PCR amplification. As shown in Table II, little or no amplified product was observed when the annealing temperature was at or above 63° C.

TABLE II

Comparison of activities at different annealing temperatures.

| Polymerase | Activity at 63° C. | Activity at 66° C. | Activity at 69° C. |
|---|---|---|---|
| Taq | 85% | 30% | <10% |
| Sso7d-ΔTaq | >95% | 70% | 40% |
| PL-ΔTaq | <5% | nd | nd |

nd: not detectable.

Example 4

Effect of Fusion Proteins on Required Primer Length

An enhancement of $T_M$ of the primers (as shown above) predicts that shorter primers could be used by Sso7d-ΔTaq, but not by Taq, to achieve efficient PCR amplification. This analysis shows that Sso7d-ΔTaq is more efficient in an assay using shorter primers compared to Taq.

Primers of different lengths were used to compare the efficiencies of PCR amplification by Sso7d-ΔTaq and by Taq. The results are shown in Table III and in FIGS. 1A-1C. When two long primers, 57F (22 mer, $T_M$=58° C.) and 732R (24 mer, $T_M$=57° C.) were used, no significant difference was observed between Sso7d-ΔTaq and Taq at either low or high annealing temperatures. When medium length primers, 57F15 (15 mer, $T_M$=35° C.) and 732R16 (16 mer, $T_m$=35° C.), were used, Sso7d-ΔTaq was more efficient than Taq, especially when the annealing temperature was high. The most striking difference between the two enzymes was observed with short primers, 57F12 (12 mer) and 732R16 (16 mer), where Sso7d-ΔTaq generated 10 times more products than Taq at both low and high annealing temperatures.

PCR using primers 57F12 (12 nt) and 732R16 (16 nt) were used to compare the efficiency of Sac7d-ΔTaq to the unmodified full length Taq in PCR reaction. Results are shown in FIG. 2. Similar to Sso7d-ΔTaq, Sac7d-ΔTaq is significantly more efficient than Taq in amplifying using short primers.

A primer length assay was used to determine the ability of PL-ΔTaq to use short primers in PCR amplification. When long primers (57F and 732R) were used, the amplified product generated by PL-ΔTaq is ~50% of that by Sso7d-ΔTaq. When short primers (57F12 and 732R16) were used, the amplified product generated by PL-ΔTaq is <20% of that by Sso7d-ΔTaq.

TABLE III

Comparison of the effect of primer length on PCR amplification by Sso7d-ΔTaq and Taq DNA polymerase.

| | 22 nt primer | | 15 nt primer | | 12 nt primer | |
|---|---|---|---|---|---|---|
| polymerase | Anneal @ 55° C. | Anneal @ 63° C. | Anneal @ 49° C. | Anneal @ 54° C. | Anneal @ 49° C. | Anneal @ 54° C. |
| Taq | 14000 | 9000 | 5500 | <500 | 1000 | undetectable |
| Sso7d-ΔTaq | 17000 | 13000 | 15000 | 5000 | 10000 | 3000 |
| Sso7d-ΔTaq:Taq | 1.2:1 | 1.4:1 | 2.7:1 | >10:1 | 10:1 | >10:1 |

Increased Performance of Fusion Polymerases in PCR Reactions

The increased stability and/or processivity of the fusion proteins of the invention provide increased efficiency in performing various modification reactions. For example, polymerase fusion proteins can provide more efficient amplification in PCR reactions. Many factors influence the outcome of a PCR reaction, including primer specificity, efficiency of the polymerase, quality, quantity and GC-content of the template, length of the amplicon, etc. Examples 5-8 demonstrate that fusion proteins that include a double-stranded sequence-non-specific nucleic acid binding domain, e.g., Sso7d, joined to a thermostable polymerase or polymerase domain have several advantageous features over the unmodified enzyme in PCR applications.

Example 5

Sso7d Fusion Proteins Exhibit a Higher and Broader Salt-tolerance in PCR

The binding of polymerase to a primed DNA template is sensitive to the ionic strength of the reaction buffer due to electrostatic interactions, which is stronger in low salt concentration and weaker in high. The presence of Sso7d in a fusion polymerase protein stabilizes the binding interaction of the polymerase to DNA template. This example demonstrates that Sso7d fusion proteins exhibit improved performance in PCR reactions containing elevated KCl concentrations.

Lambda DNA (2 pM) was used as a template in a PCR reactions with primers 57F and 732R. The concentration of KCl was varied from 10 mM to 150 mM, while all other components of the reaction buffer were unchanged. The PCR reaction was carried out using a cycling program of 94° C. for 3 min, 20 cycles of 94° C. for 30 sec, 55° C. for 30 sec, and 72° C. for 30 sec, followed by 72° C. for 10 min. Upon completion of the reaction, 5 μl of the PCR reaction was removed and mixed with 195 μl of 1:400 dilution of PicoGreen in TE to quantify the amounts of amplicon generated. The PCR reaction products were also analyzed in parallel on an agarose gel to verify that amplicons of expected length were generated (data not shown). The effects of KCl concentration on the PCR efficiency of Sso7d-ΔTaq versus that of ΔTaq, and Pfu-Sso7d versus Pfu are shown in Table IV. The unmodified enzymes, ΔTaq and Pfu, showed a preference for KCl concentration below 25 mM and 40 mM, respectively, to maintain 80% of the maximum activity. In contrast, fusion proteins Sso7d-ΔTaq and Pfu-Sso7d maintain 80% of the maximum activity in 30-100 mM and 60-100 mM KCl, respectively. Thus, the Sso7d fusion proteins were more tolerant of elevated KCl concentration in comparison to their unmodified counter parts. This feature of the hybrid polymerase will potentially allow PCR amplification from low quality of DNA template, e.g., DNA samples prepared from, but not limited to, blood, food, and plant sources.

TABLE IV

Sso7d modification increases salt-tolerance of polymerase in PCR reaction

| Enzyme | Enzyme concentration | [KCl] for 80% activity |
|---|---|---|
| ΔTaq | 20 U/ml | <25 mM |
| Sso7d-ΔTaq | 20 U/ml | 30-100 mM |
| Pfu | 3 U/ml | <40 mM |
| Pfu-Sso7d | 12 U/ml* (equal molar) | 60-100 mM |

*Pfu-Sso7d has a 4-fold higher specific activity than Pfu. The specific activity is defined as unit/mol of enzyme.

Example 6

Sso7d Fusion Polymerases Require Shorter Extension Time in PCR

The processivity of a polymerase directly effects the efficiency of the polymerization step. For example, a polymerase with low processivity dissociates more frequently and requires more time to rebind to the primed-template, whereas a polymerase with high processivity requires fewer binding events to complete replication of the entire template. As demonstrated in Example 2, Sso7d fusion proteins have significantly higher processivity than their unmodified counterparts. Thus, the fusion proteins should be more efficient during the primer extension step of a PCR reaction. Here we provide examples demonstrating that an Sso7d fusion polymerase requires a shorter extension time to amplify a large fragment during PCR compared to unmodified polymerases. In addition, we show that a single enzyme fusion polymerase exhibits an enhanced ability to amplify large DNA fragments in a limited amount of time in comparison to an enzyme mixture (DyNAzyme EXT) currently used in the art for amplification of large fragments.

Example 6-1

Sso7d Fusion Polymerases Require Shorter Extension Time in PCR

Lambda DNA (2.25 pM) was used as a PCR template. Three pairs of primers L71F (5'-CCTGCTCTGCCGCTTCACGC-3'; SEQ ID NO:13) and L71R (5'-GCACAGCGGCTGGCTGAG GA-3'; SEQ ID NO:14), L18015F (5'-TGACGGAGGATAACGCCAGCAG-3'; SEQ ID NO:15) and L23474R (5'-GAAAGACGA TGGGTCGCTAATACGC-3'; SEQ ID NO:16), and L18015F (5'-TGACGGAGGATAAC GCCAGCAG-3'; SEQ ID NO:17) and L29930R (5'-GGGGTTGGAGGT-CAATGGGTTC-3'; SEQ ID NO:18), were used to amplify DNA fragments of the size of 0.9 kb, 5.5 kb and 11.9 kb, respectively. Each reaction contained 40 unit/ml of polymerase, where the unit was defined as described in Example 2, and 0.36 mM of each of the four dNTPs. The reaction buffer used for Pfu (from Stratagene) contained 20 mM Tris-HCl (pH 8.8), 2 mM $MgSO_4$, 10 mM KCl, 10 mM $(NH_4)_2SO_4$, 0.1% Triton X-100, and 0.1 mg/ml BSA. The reaction buffer for Pfu-Sso7d, Taq, and Sso7d-Taq was the above buffer with an additional 40 mM of KCl. Two cycling programs with a 1 mm or a 5 mm extension time were used for PCR amplification. Each cycling program was composed of 94° C. for 20 sec, hot start at 80° C. by the addition of the polymerase, 20 cycles of 94° C. for 10 sec followed by 72° C. for 1 or 5 min, and 72° C. for 5 min. The results showed that a Pfu-Sso7d fusion protein was able to amplify both the 1 kb and 5 kb fragments using a 1 min extension time, and was also able to amplify the 10 kb fragment using a 5 min extension time. In contrast, Pfu polymerase amplified only the 1 kb fragment using either a 1 min or a 5 min extension time. Similarly, the Sso7d-Taq fusion protein amplified the 1 kb fragment using a 1 min extension time, and both the 1 kb and 5 kb fragments with a 5 min extension time, whereas Taq polymerase amplified only the 1 kb fragment with a 5 min extension time.

Thus, the presence of Sso7d in the fusion protein results in shorter extension times in PCR reactions compared to the unmodified protein.

Example 6-2

Pfu-Sso7d Fusion Polymerase Outperforms Existing Long PCR Enzyme Mixture

Currently, PCR amplification of long DNA fragments requires the use of an enzyme mixture containing both a non-proofreading polymerase (e.g. Taq or DyNAzyme II) and a small amount of proofreading polymerase (e.g. Pfu or Deep Vent). We have compared a single fusion enzyme, Pfu-Sso7d, to one of the high performance, long PCR enzymes DyNAzyme EXT (from Finnzymes) in long PCR, and demonstrated that Pfu-Sso7d outperforms DyNAzyme EXT, especially with limited extension time.

Lambda DNA (2.25 pM) was used as a PCR template. Four pairs of primers L71F (5'-CCTGCTCTGCCGCTTCACGC-3'; SEQ ID NO:13) and L71R (5'-GCACAGCGGCTGGCT-GAG SEQ ID NO:14), L30350F (5'-CCTGCTCTGCCGCT-TCACGC-3'; SEQ ID NO:19) and L35121R (5'-CACATGGTACAGCAAGCCTGGC-3'; SEQ ID NO:20), L2089F (5'-CCCGTATCTGCTGGGATACTGGC-3'; SEQ ID NO:21) and L7112R (5'-CAGCGGTGCTGACTGAAT-CATGG-3'; SEQ ID NO:22), and L30350F (5'-CCTGCCT-GCCGCTTCACGC-3'; SEQ ID NO:23) and L40547R (5'-CCAATACCCGTTTCA TCGCGGC-3'; SEQ ID NO:24) were used to amplify DNA fragments of the size of 0.9 kb, 4.8 kb, 5.0 kb and 10.2 kb, respectively. Four concentrations (10 unit/ml, 20 unit/ml, 40 unit/ml and 80 unit/ml) of Pfu-Sso7d were used, and two concentrations (20 unit/ml and 40 unit/ml) of DyNAzyme EXT were used. Each reaction contained 0.36 mM of each of the four dNTPs. The reaction buffer for Pfu-Sso7d was as described in Example 6-1. The reaction buffer for DyNAzyme EXT contained 20 mM Tris (pH 9.0), 2 mM $MgCl_2$, 15 mM $(NH_4)_2SO_4$, and 0.1% Triton X -100 (provided by Finnzymes). All reaction components were first mixed on ice, and the reactions were initiated by placing the sample plates into a thermal cycler (MJ Research) preheated to over 90° C. The PCR cycling program consists of 95° C. for 20 sec, 20 cycles of 94° C. for 10 sec and 70° C. for 1 or 1.5 min, and 1 cycle of 72° C. for 10 min.

Thus, the fusion polymerase Pfu-Sso7d is notably more efficient as a single enzyme than an enzyme mixture such as DyNAzyme EXT in long PCR.

Example 7

Sso7d Fusion Proteins are more Sensitive in PCR Amplification

This example demonstrates that an Sso7d fusion polymerase can amplify a target that is present at a lower copy number compared to the unmodified polymerases. Plasmid DNA was used as a PCR template with T3 and T7 as the primers, which amplify a 500 bp fragment. The amount of plasmid DNA was varied so that the number of copies of DNA template present in the PCR reaction ranged from $10^8$ to 1. The cycling program was 94° C. for 3 min, 25 or 35 cycles of 96° C. for 1 sec, 50° C. for 15 sec, and 68° C. for 30 sec, followed by 1 cycle at 68° C. for 5 min. For template copy numbers from $10^4$ to $10^8$ (per 25 µl reaction), 25 cycles of amplification were performed; for template copy numbers from 1 to $10^4$ (per 25 µl reaction), 35 cycles of amplification were performed.

The Sso7d fusion polymerase was compared to the unmodified polymerase in the requirements for minimum copies of template for efficient amplification. As shown in Table V, Pfu-Sso7d is significantly more sensitive than Pfu in its ability to amplify a low copy number of DNA template, showing that fusion polymerase of the invention can increase the sensitivity of PCR reactions by as much as five orders of magnitude.

TABLE V

Sso7d fusion protein can amplify using a lower number of copies of DNA template

| Enzymes | Minimum copies for amplification |
|---|---|
| Pfu | $>10^7$ |
| Pfu-Sso7d | $10^2$ |

Example 8

Sso7d Fusion Polymerases Maintain High Specificity in a PCR Reaction

As shown in Example 3, Sso7d-ΔTaq fusion protein stabilizes primer-template interactions, as reflected by its ability to allow higher annealing temperature and/or shorter primers in PCR amplification. To assess whether this property of the fusion protein would result in nonspecific amplification in PCR, a complex DNA template (e.g human genomic DNA) was used as the target template. The following two examples demonstrate that the specificity of amplification achieved using Pfu-Sso7d is no less than that Taq, the most commonly used PCR enzyme.

Example 8-1

Amplification of a Gender-specific Marker from Human DNA using Pfu-Sso7d

Human female or male type DNA (concentration, 1 fM) from placenta or chorionic tissue (from Sigma) was used as the template. Primers H-Amelo-Y (5'-CCACCTCATC-CTGG GCACC-3'; SEQ ID NO:25) and H-Amelo-YR (5'-GCTTGAGGCCAACCATCA GAGC-3'; SEQ ID NO:26) were used to amplify a 212 bp amplicon from X chromosome and a 218 bp amplicon from Y chromosome. A single 212 bp fragment should be amplified from female typed DNA, whereas three fragments (212 bp, 218 bp, and the 212 bp/218 bp heterozygote) were expected from male typed DNA. Each reaction contained 20 unit/ml of polymerase and 0.36 mM of each of the four dNTPs. The reaction buffer for Taq included 10 mM Tris (pH 8.8), 50 mM KCl, 1.5 mM MgCl2 and 0.1% Triton X-100 (provided by Amersham). The reaction buffer for Pfu-Sso7d contains was performed using DyNAzyme EXT buffer (see Example 6-2) with an additional 40 mM KCl. All reaction components were mixed on ice, and the reaction was initiated by placing the plates into a thermal cycler preheated to above 65° C. The cycling program consisted of 95° C. for 2 min, 30 cycles of 94° C. for 5 sec, 64° C. for 10 sec, and 72° C. for 10 sec, followed by 1 cycle of 7 min at 72° C. Specific amplicons of expected sizes were amplified by both Pfu-Sso7d and Taq polymerase.

Example 8-2

Amplification of β-Globin Gene from Human DNA using Pfu-Sso 7d

Human DNA (1 fM) from placenta or chorionic tissue (from Sigma) was used as the template. Three pairs of primers, Bglbn536F (5'-GGTTGGCCAATCTA CTCCCAGG-3'; SEQ ID NO:27) and Bglbn536R (5'-GCTCACTCAGTGTG-GCAAAG-3'; SEQ ID NO:28), Bglbn536F and Bglbn1083R, and Bglbn536F and Bglbn1408R (5'-GATTAG-CAAAAGGGCCTAGCTTGG-3'; SEQ ID NO:29) were used to amplify DNA fragments of the size of 0.5, 1.1 and 1.4 kb, respectively. Each reaction contained 20 unit/ml of polymerase and 0.36 mM of each of the four dNTPs. The reaction buffers for Taq and Pfu-Sso7d were as described in Example 8-1. All reaction components were first mixed on ice, and the reactions were initiated by placing the plates into a thermal cycler preheated to above 65° C. The cycling program consists of 95° C. for 2 min, 30 cycles of 94° C. for 45 sec, 64° C. for 45 sec, and 72° C. for 1 min, followed by 1 cycle of 7 min at 72° C. With each of the three pair of primers used, an amplified product of the expected size was produced using Pfu-Sso7d. These results show that the specificity of amplification achieved by using Pfu-Sso7d is equal or better than that with Taq polymerase.

Sequence Listing

SEQ ID NO:1 Synthetic Sso7d gene

GCAACCGTAAAGTTCAAGTACAAAGGC-GAAGAAAAAGAGGTAGACATCTCCAA GATCAA-GAAAGTATGGCGTGTGGGCAAGAT-GATCTCCTTCACCTACGACGAGGG CGGTGGCAAGACCGGCCGTGGTGCGG-TAAGCGAAAAGGACGCGCCGAAGGAGC TGCTG-CAGATGCTGGAGAAG CAGAAAAAG

SEQ ID NO:2 The amino acid sequence of Sso7d.

ATVKFKYKGEEKEVDISKIKKVWRVGKM-ISFTYDEGGGKTGRGAVSEKDAPKELLQ MLE-KQKK

SEQ ID NO:3 The DNA sequence encoding the Sso7d-ΔTaq fusion protein

ATGATTACGAATTCGAGCGCAACCG-TAAAGTTCAAGTACAAAGGCGAAGAAAAA GAG-GTAGACATCTCCAAGATCAAGAAAG-TATGGCGTGTGGGCAAGATGATCTCC TTCACCTACGACGAGGGCGGTGGCAA-GACCGGCCGTGGTGCGGTAAGCGAAAAG GACGCGCCGAAGGAGCTGCTGCAGAT-GCTGGAGAAGCAGAAAAAGGGCGGCGG TGT-CACTAGTCCCAAGGCcCTGGAGGAGGC-CCCCTGGCCCCCGCCGGAAGGGGCC TTCGTGGGCTTTGTGCTTTCCCGCAAG-GAGCCCATGTGGGCCGATCTTCTGGCCCT GGC-CGCCGCCAGGGGGGGCCGGGTCCAC-CGGGCCCCCGAGCCTTATAAAGCCCT CAGGGACCTGAAGGAGGCGCGGGGGCT-TCTCGCCAAAGACCTGAGCGTTCTGGC CCT-GAGGGAAGGCCTTGGCCTCCCGCCCGGC-GACGACCCCATGCTCCTCGCCTAC CTCCTGGACCCTTCCAACACCAC-CCCCGAGGGGGTGGCCCGGCGCTACGGCGGG GAGTGGACGGAGGAGGCGGGG-GAGCGGGCCGCCCTTTCCGAGAGGCTCTTCGCC AACCTGTGGGGGAGGCTTGAGGGGGAG-GAGAGGCTCCTTTGGCTTTACCGGGAG GTG-GAGAGGCCCCTTTCCGCTGTCCTGGC-CCACATGGAGGCCACGGGGGTGCGC CTGGACGTGGCCTATCTCAGGGCCT-TGTCCCTGGAGGTGGCCGAGGAGATCGCCC GCCTCGAGGCCGAGGTCTTCCGCCTGGC-CGGCCACCCCTTCAACCTCAACTCCCG GGAC-CAGCTGGAAAGGGTCCTCTTTGAC-GAGCTAGGGCTTCCCGCCATCGGCAA GACGGAGAAGACCGGCAAGCGCTCCAC-CAGCGCCGCCGTCCTGGAGGCCCTCCG CGAG-GCCCACCCCATCGTGGAGAAGATCCTG-CAGTACCGGGAGCTCACCAAGCT GAAGAGCACCTACATTGACCCCTTGCCG-GACCTCATCCACCCCAGGACGGGCCG CCTCCA-CACCCGCTTCAACCAGACGGCCACGGC-CACGGGCAGGCTAAGTAGCTC CGATCCCAACCTCCAGAACATCCCCGTC-CGCACCCCGCTTGGGCAGAGGATCCGC CGGGC-CTTCATCGCCGAGGAGGGGTGGCTATTG-GTGGCCCTGGACTATAGCCAG ATAGAGCTCAGGGTGCTGGCCCAC-CTCTCCGGCGACGAGAACCTGATCCGGGTCT TCCAGGAGGGGCGGGACATCCACACG-GAGACCGCCAGCTGGATGTTCGGCGTCC CCCGG-GAGGCCGTGGACCCCCTGATGCGC-CGGGCGGCCAAGACCATCAACTTCG GGGTCCTCTACGGCATGTCGGCCCAC-CGCCTCTCCCAGGAGCTAGCCATCCCTTA CGAG-GAGGCCCAGGCCTTCATTGAGCGC-TACTTTCAGAGCTTCCCCAAGGTGCGG GCCTGGATTGAGAAGACCCTGGAG-GAGGGCAGGAGGCGGGGGTACGTGGAGAC

CCTCTTCGGCCGCCGCCGCTACGTGCCA-GACCTAGAGGCCCGGGTGAAGAGCGT GCGG-GAGGCGGCCGAGCGCATGGCCTTCAA-CATGCCCGTCCAGGGCACCGCCGC CGACCTCATGAAGCTGGCTATGGT-GAAGCTCTTCCCCAGGCTGGAGGAAATGGG GGCCAGGATGCTCCTTCAGGTCCACGAC-GAGCTGGTCCTCGAGGCCCCAAAAGA GAGGGCGGAGGCCGTGGCCCGGCTGGC-CAAGGAGGTCATGGAGGGGGTGTATCC CCTGGC-CGTGCCCCTGGAGGTGGAGGTGGGGAT-AGGGGAGGACTGGCTCTCCGC CAAGGAGGGCATTGATGGCCGCGGCG-GAGGCGGGCATCATCATCATCATCATTA A

SEQ ID NO:4 The amino acid sequence of Sso7d-ΔTaq fusion protein

MITNSSATVKFKYKGEEKEVDIS-KIKKVWRVGKMISFTYDEGGGKTGRGAVSEKDA PKELLQMLEKQKKGGGVTSPKALEEAPW-PPPEGAFVGFVLSRKEPMWADLLALAA ARG-GRVHRAPEPYKALRDLKEARGLLAKDLS-VLALREGLGLPPGDDPMLLAYLLDP SNTTPEGVARRYGGEWTEEAGERAAL-SERLFANLWGRLEGEERLLWLYREVERPLS AVLAHMEATGVRLDVAYLRALSLEVAEE-IARLEAEVFRLAGHPFNLNSRDQLERVLF DEL-GLPAIGKTEKTGKRSTSAAVLEALREAH-PIVEKILQYRELTKLKSTYIDPLPDLIH PRTGRLHTRFNQTATATGRLSSSDPN-LQNIPVRTPLGQRIRRAFIAEEGWLLVALDYS QIEL-RVLAHLSGDENLIRVFQEGRDIHTETA-SWMFGVPREAVDPLMRRAAKTINFGV LYGMSAHRLSQELAIPYEEAQAFIERY-FQSFPKVRAWIEKTLEEGRRRGYVETLFGRR RYVPDLEARVKSVREAAERMAFNMPVQG-TAADLMKLAMVKLFPRLEEMGARMLL QVH-DELVLEAPKERAEAVARLAKEVMEGVY-PLAVPLEVEVGIGEDWLSAKEGIDGR GGGGHHHHHH

SEQ ID NO:5 The DNA sequence encoding the Sso7d-Taq fusion protein

ATGATTACGAATTCGAGCGCAACCG-TAAAGTTCAAGTACAAAGGCGAAGAAAAA GAG-GTAGACATCTCCAAGATCAAGAAAG-TATGGCGTGTGGGCAAGATGATCTCC TTCACCTACGACGAGGGCGGTGGCAA-GACCGGCCGT GGTGCGGTAAGCGAAAAG GACGCGCCGAAGGAGCTGCTGCAGAT-GCTGGAGAAGCAGAAAAAGGGCGGCGG TGT-CACTAGTGGGATGCTGC-CCCTCTTTGAGCCCAAGGGCCGGGTCCTCCTGGTG GACGGCCACCACCTGGCCTACCGCACCT-TCCACGCCCTGAAGGGCCTCACCACCA GCCGGGGGGAGCCGGTGCAGGCGGTC-TACGGCTTCGCCAAGAGCCTCCTCAAGG CCCT-CAAGGAGGACGGGGACGCGGTGATCGTG-GTCTTTGACGCCAAGGCCCCCT CCTTCCGCCACGAGGCCTACGGGGGGTA-CAAGGCGGGCCGGGCCCCCACGCCAG AGGACTTTCCCCGGCAACTCGCCCTCAT-CAAGGAGCTGGTGGACCTCCTGGGGCT GGCGCGCCTCGAGGTCCCGGGCTACGAG-GCGGACGACGTCCTGGCCAGCCTGGC CAA-GAAGGCGGAAAAGGAGGGCTACGAGGTC-CGCATCCTCACCGCCGACAAAG ACCTTTACCAGCTCCTTTCCGACCG-CATCCACGTCCTCCACCCCGAGGGGTACCT CAT-CACCCCGGCCTGGCTTTGGGAAAAG-TACGGCCTGAGGCCCGACCAGTGGGC CGACTACCGGGCCCTGACCGGGGAC-GAGTCCGACAACCTTCCCGGGGTCAAGGG CATCGGGGAGAAGACGGCGAGGAAGCT-TCTGGAGGAGTGGGGGAGCCTGGAAG CCCTCCT-CAAGAACCTGGACCGGCTGAAGCCCGC-CATCCGGGAGAAGATCCTGG CCCACATGGACGATCTGAAGCTCTC-CTGGGACCTGGCCAAGGTGCGCACCGACCT GCCCCTGGAGGTGGACTTCGCCAAAAGGC GGGAGCCCGACCGGGAGAGGCTTAG GGC-CTTTCTGGAGAGGCTTGAGTTTGGCAGC-CTCCTCCACGAGTTCGGCCTTCTG GAAAGC-CCCAAGGCcCTGGAGGAGGCCCCCTGGCCCCCG-CCGGAAGGGGCCTTC GTGGGCTTTGTGCTTTC-CCGCAAGGAGCCCATGTGGGCCGATCT-TCTGGCCCTGG CCGCCGCCAGGGGGGGC-CGGGTCCACCGGGCCCCCGAGCCTTATAAAGC-CCTCA GGGACCTGAAGGAGGCGCGGGGGCT-TCTCGCCAAAGACCTGAGCGTTCTGGCCC TGAGGGAAGGCCTTGGCCTCCCGCCCG-GCGACGACCCCATGCTCCTCGCCTACCT CCTG-GACCCTTCCAACACCAC-CCCCGAGGGGGTGGCCCGGCGCTACGGCGGGGA GTGGACGGAGGAGGCGGGGGAGCGGGC-CGCCCTTTCCGAGAGGCTCTTCGCCAA CCT-GTGGGGGAGGCTTGAGGGGGAGGAGAG-GCTCCTTTGGCTTTACCGGGAGGT GGAGAGGCCCCTTTCCGCTGTCCTGGC-CCACATGGAGGCCACGGGGGTGCGCCT GGACGTGGCCTATCTCAGGGCCTTGTC-CCTGGAGGTGGCCGAGGAGATCGCCCG CCTC-GAGGCCGAGGTCTTCCGCCTGGCCGGC-CACCCCTTCAACCTCAACTCCCGG GACCAGCTGGAAAGGGTCCTCTTTGAC-GAGCTAGGGCTTCCCGCCATCGGCAAG ACG-GAGAAGACCGGCAAGCGCTCCAC-CAGCGCCGCCGTCCTGGAGGCCCTCCGC GAGGCCCACCCCATCGTGGAGAAGATC-CTGCAGTACCGGGAGCTCACCAAGCTG AAGAG-CACCTACATTGACCCCTTGCCGGACCT-CATCCACCCCAGGACGGGCCGCC TCCACACCCGCTTCAACCAGACGGC-CACGGCCACGGGCAGGCTAAGTAGCTCCG ATC-CCAACCTCCAGAACATCCCCGTCCGCAC-CCCGCTTGGGCAGAGGATCCGCCG GGCCTTCATCGCCGAGGAGGGGTGGC-TATTGGTGGCCCTGGACTATAGCCAGAT AGAGCT-CAGGGTGCTGGCCCACCTCTCCGGCGAC-GAGAACCTGATCCGGGTCTTC CAGGAGGGGCGGGACATCCACACG-GAGACCGCCAGCTGGATGTTCGGCGTCCCC CGG-GAGGCCGTGGACCCCCTGATGCGC-CGGGCGGCCAAGACCATCAACTTCGGG GTCCTCTACGGCATGTCGGCCCACCGC-CTCTCCCAGGAGCTAGCCATCCCTTACG AGGAG-GCCCAGGCCTTCATTGAGCGC-TACTTTCAGAGCTTCCCCAAGGTGCGGGC CTGGATTGAGAAGACCCTGGAG-GAGGGCAGGAGGCGGGGGTACGTGGAGACCC TCTTCGGCCGCCGCCGCTACGTGCCA-GACCTAGAGGCCCGGGTGAAGAGCGTGC GGGAGGCGGCCGAGCGCATGGCCTTCAA-CATGCCCGTCCAGGGCACCGCCGCCG ACCTCAT-GAAGCTGGCTATGGTGAAGCTCTTC-

CCCAGGCTGGAGGAAATGGGGG CCAGGATGCTCCTTCAGGTCCACGAC-GAGCTGGTCCTCGAGGCCCCAAAAGAGA GGGCGGAGGCCGTGGCCCGGCTGGC-CAAGGAGGTCATGGAGGGGGTGTATCCCC TGGC-CGTGCCCCTGGAGGTGGAGGTGGGGAT-AGGGGAGGACTGGCTCTCCGCCA AGGAGGGCATTGATGGCCGCGGCGGAG-GCGGGCATCATCATCATCATCATTAA

SEQ ID NO:6 The amino acid sequence of Sso7d-Taq fusion protein.

MITNSSATVKFKYKGEEKEVDIS-KIKKVWRVGKMISFTYDEGGGKTGRGAVSEKDA PKELLQMLEKQKKGGGVTSGMLPLFEP-KGRVLLVDGHHLAYRTFHALKGLTTSRGE PVQAVYGFAKSLLKALKEDGDAVIV-VFDAKAPSFRHEAYGGYKAGRAPTPEDFPRQ LALIKELVDLLGLARLEVPGYEADDV-LASLAKKAEKEGYEVRILTADKDLYQLLSDR IHV-LHPEGYLITPAWLWEKYGLRP-DQWADYRALTGDESDNLPGVKGIGEKTARKLL EEWGSLEALLKNLDRLKPAIREKILAHM-DDLKLSWDLAKVRTDLPLEVDFAKRREP DRERL-RAFLERLEFGSLLHEFGLLESPKALEE-APWPPPEGAFVGFVLSRKEPMWADL LALAAARGGRVHRAPEPYKALRDLKEAR-GLLAKDLSVLALREGLGLPPGDDPMLLA YLL-DPSNTTPEGVARRYGGEWTEEAGER-AALSERLFANLWGRLEGEERLLWLYREV ERPLSAVLAHMEATGVRLDVAYLRALSL-EVAEEIARLEAEVFRLAGHPFNLNSRDQL ERV-LFDELGLPAIGKTEKTGKRSTSAAV-LEALREAHPIVEKILQYRELTKLKSTYIDPL PDLIHPRTGRLHTRFNQTATATGRLSSS-DPNLQNIPVRTPLGQRIRRAFIAEEGWLLVA LDYS-QIELRVLAHLSGDEN-LIRVFQEGRDIHTETASWMFGVPREAVDPLMRRA-AKTI NFGVLYGMSAHRLSQELAIPYEEAQAFI-ERYFQSFPKVRAWIEKTLEEGRRRGYVETL FGR-RRYVPDLEARVKSVREAAERMAFN-MPVQGTAADLMKLAMVKLFPRLEEMGA RMLLQVHDELVLEAPKERAEAVAR-LAKEVMEGVYPLAVPLEVEVGIGEDWLSAKE GIDGRGGGGHHHHHH

SEQ ID NO:7 The DNA sequence encoding the Pfu-Sso7d fusion protein

ATGATTTTAGATGTGGATTACATAACT-GAAGAAGGAAAACCTGTTATTAGGCTAT TCAAAAAAGAGAACGGAAAATTTAA-GATAGAGCATGATAGAACTTTTAGACCAT ACATT-TACGCTCTTCTCAGGGATGATTCAAA-GATTGAAGAAGTTAAGAAAATAAC GGGGGAAAGGCATGGAAAGATTGT-GAGAATTGTTGATGTAGAGAAGGTTGAGAA AAAGTTTCTCGGCAAGCCTATTACCGT-GTGGAAACTTTATTTGGAACATCCCCAA GATGT-TCCCACTATTAGAGAAAAAGTTAGAGAA-CATCCAGCAGTTGTGGACATCT TCGAATACGATATTCCATTTGCAAA-GAGATACCTCATCGACAAAGGCCTAATACC AATG-GAGGGGGAAGAAGAGCTAAAGATTCT-TGCCTTCGATATAGAAACCCTCTA TCACGAAGGAGAAGAGTTTGGAAAAGGC-CCAATTATAATGATTAGTTATGCAGA TGAAAAT-GAAGCAAAGGTGATTACTTGGAAAAA-CATAGATCTTCCATACGTTGA GGTTGTATCAAGCGAGAGAGAGAT-GATAAAGAGATTTCTCAGGATTATCAGGGA GAAGGATCCTGACATTATAGTTACT-TATAATGGAGACTCATTCGACTTCCCATAT TTAGC-GAAAAGGGCAGAAAAACTTGGGAT-TAAATTAACCATTGGAAGAGATGGA AGCGAGCCCAAGATGCAGAGAATAGGC-GATATGACGGCTGTAGAAGTCAAGGG AAGAATA-CATTTCGACTTGTATCATGTAATAA-CAAGGACAATAAATCTCCCAACA TACACACTAGAGGCTGTATATGAAG-CAATTTTTGGAAAGCCAAAGGAGAAGGTA TACGCCGACGAGATAGCAAAAGCCTGG-GAAAGTGGAGAGAACCTTGAGAGAGTT GCCAAATACTCGATGGAAGATGCAAAG-GCAACTTATGAACTCGGGAAAGAATTC CTTC-CAATGGAAATTCAGCTTTCAAGATTAGT-TGGACAACCTTTATGGGATGTTT CAAGGTCAAGCACAGGGAACCTTGTA-GAGTGGTTCTTACTTAGGAAAGCCTACG AAA-GAAACGAAGTAGCTCCAAACAAGC-CAAGTGAAGAGGAGTATCAAAGAAGG CTCAGGGAGAGCTACACAGGTGGAT-TCGTTAAAGAGCCAGAAAAGGGGTTGTGG GAAAACATAGTATACCTAGATTTTA-GAGCCCTATATCCCTCGATTATAATTACCC ACAAT-GTTTCTCCCGATACTCTAAATCTTGAGG-GATGCAAGAACTATGATATCGC TCCTCAAGTAGGCCACAAGTTCTGCAAG-GACATCCCTGGTTTTATACCAAGTCTC TTGGGA-CATTTGTTAGAGGAAAGACAAAAGAT-TAAGACAAAAATGAAGGAAACT CAAGATCCTATAGAAAAAATACTCCT-TGACTATAGACAAAAAGCGATAAAACTC TTAG-CAAATTCTTTCTACGGATATTATGGC-TATGCAAAAGCAAGATGGTACTGTA AGGAGTGTGCTGAGAGCGTTACTGC-CTGGGGAAGAAAGTACATCGAGTTAGTAT GGAAGGAGCTCGAAGAAAAGTTTGGATT-TAAAGTCCTCTACATTGACACTGATG GTCTCTAT-GCAACTATCCCAGGAGGAGAAAGTGAG-GAAATAAAGAAAAAGGCTC TAGAATTTGTAAAATACATAAAT-TCAAAGCTCCCTGGACTGCTAGAGCTTGAATA TGAAGGGTTTTATAAGAGGGGATTCT-TCGTTACGAAGAAGAGGTATGCAGTAAT AGAT-GAAGAAGGAAAAGTCATTACTCGTGGTT-TAGAGATAGTTAGGAGAGATTG GAGTGAAATTGCAAAAGAAACT-CAAGCTAGAGTTTTGGAGACAATACTAAAACA CGGAGATGTTGAAGAAGCTGTGAGAAT-AGTAAAAGAAGTAATACAAAAGCTTGC CAATTAT-GAAATTCCACCAGAGAAGCTCG-CAATATATGAGCAGATAACAAGACC ATTACATGAGTATAAGGCGATAGGTCCT-CACGTAGCTGTTGCAAAGAAACTAGCT GCTAAAGGAGTTAAAATAAAGCCAG-GAATGGTAATTGGATACATAGTACTTAGA GGC-GATGGTCCAATTAGCAATAGGGCAAT-TCTAGCTGAGGAATACGATCCCAAA AAGCACAAGTATGACGCAGAATATTA-CATTGAGAACCAGGTTCTTCCAGCGGTA CTTAG-GATATTGGAGGGATTTGGATACAGAAAG-GAAGACCTCAGATACCAAAAG ACAAGACAAGTCGGCCTAACTTCCTG-GCTTAACATTAAAAAATCCGGTACCGGC GGTG-GCGGTGCAACCGTAAAGTTCAAGTA-

CAAAGGCGAAGAAAAAGAGGTAGA CATCTCCAAGATCAAGAAAGTATGGCGT-GTGGGCAAGATGATCTCCTTCACCTAC GAC-GAGGGCGGTGGCAAGACCGGCCGTGGT-GCGGTAAGCGAAAAGGACGCGCC GAAGGAGCTGCTGCAGATGCTGGAGAAG-CAGAAAAAGTGA

SEQ ID NO:8 The amino acid sequence of the Pfu-Sso7d fusion protein

MILDVDYITEEGKPVIRLFKKENGKFK-IEHDRTFRPYIYALLRDDSKIEEVKKITGERH GKIVRIVDVEKVEKKFLGKPITVWK-LYLEHPQDVPTIREKVREHPAVVDIFEYDIPFA KRYLIDKGLIPMEGEEELKILAFDIET-LYHEGEEFGKGPIIMISYADENEAKVITWKNID LPYVEVVS SEREMIKRFLRIIREKDPDIIVTYNGDS-FDFPYLAKRAEKLGIKLTIGRDGS EPKMQRIGD-MTAVEVKGRIHFDLYHVITRTINLP-TYTLEAVYEAIFGKPKEKVYADEI AKAWESGENLERVAKYSMEDAKATYEL-GKEFLPMEIQLSRLVGQPLWDVSRSSTGN LVEW-FLLRKAYERNEVAPNKPSEEEYQRRLR-ESYTGGFVKEPEKGLWENIVYLDFR ALYPSIIITHNVSPDTLNLEGCKNYDI-APQVGHKFCKDIPGFIPSLLGHLLEERQKIKTK MKETQDPIEKILLDYRQKAIKLLANS-FYGYYGYAKARWYCKECAESVTAWGRKYIE LVWKELEEKFGFKVLYIDTDGLYATIPG-GESEEIKKKALEFVKYINSKLPGLLELEYE GFYKRGFFVTKKRYAVIDEEGKVITR-GLEIVRRDWSEIAKETQARVLETILKHGDVEE AVRIVKEVIQKLANYEIPPEKLAIYE-QITRPLHEYKAIGPHVAVAKKLAAKGVKIKPG MVI-GYIVLRGDGPISNRAILAEEYDPKKHKY-DAEYYIENQVLPAVLRILEGFGYRKED LRYQKTRQVGLTSWLNIKKSGTGGG-GATVKFKYKGEEKEVDISKIKKVWRVGKMIS FTY-DEGGGKTGRGAVSEKDAPKELLQMLEKQKK

SEQ ID NO:9 The DNA sequence encoding the Sac7d-ΔTaq fusion protein

ATGATTACGAATTCGACGGTGAAGG-TAAAGTTCAAGTATAAGGGTGAAGAGAAA GAAG-TAGACACTTCAAAGATAAAGAAGGTTTG-GAGAGTAGGCAAAATGGTGTCC TTTACCTATGACGACAATGGTAAGACAG-GTAGAGGAGCTGTAAGCGAGAAAGAT GCTC-CAAAAGAATTATTAGACATGTTAGCAA-GAGCAGAAAGAGAGAAGAAAGG CGGCGGTGTCACTAGTCCCAAGGCCCTG-GAGGAGGCCCCCTGGCCCCCGCCGGA AGGGGC-CTTCGTGGGCTTTGTGCTTTCCCGCAAG-GAGCCCATGTGGGCCGATCTT CTGGCCCTGGCCGCCGCCAGGGGGGGC-CGGGTCCACCGGGCCCCCGAGCCTTAT AAAGC-CCTCAGGGACCTGAAGGAG-GCGCGGGGGCTTCTCGCCAAAGACCTGAGC GTTCTGGCCCTGAGGGAAGGCCTTGGC-CTCCCGCCCGGCGACGACCCCATGCTCC TCGC-CTACCTCCTGGACCCTTCCAACACCAC-CCCCGAGGGGGTGGCCCGGCGCTA CGGCGGGGAGTGGACGGAGGAGGCGGGG-GAGCGGGCCGCCCTTTCCGAGAGGC TCTTCGC-CAACCTGTGGGGGAGGCTTGAGGGGGAG-GAGAGG CTCCTTTGGCTTTA CCGGGAGGTGGAGAGGCCCCTTTCCGCT-GTCCTGGCCCACATGGAGGCCACGGG GGT-GCGCCTGGACGTGGCCTATCTCAGGGC-CTTGTCCCTGGAGGTGGCCGAGGA GATCGCCCGCCTCGAGGCCGGGTCTTC-CGCCTGGCCGGCCACCCCTTCAACCTCA ACTC-CCGGGACCAGCTGGAAAGGGTC-CTCTTTGACGAGCTAGGGCTTCCCGCCAT CGGCAAGACGGAGAAGACCG-GCAAGCGCTCCACCAGCGCCGCCGTC-CTGGAGGC CCTCCGCGAGGCCCACCCCATCGTG-GAGAAGATCCTGCAGTACCGGGAGCTCAC CAAGCTGAAGAGCACCTACATTGAC-CCCTTGCCGGACCTCATCCACCCCAGGACG GGC-CGCCTCCACACCCGCTTCAACCAGACG-GCCACGGCCACGGGCAGGCTAAGT AGCTCCGATCCCAACCTCCAGAACATC-CCCGTCCGCACCCCGCTTGGGCAGAGGA TCCGC-CGGGCCTTCATCGCCGAGGAGGGGTGGC-TATTGGTGGCCCTGGACTATAG CCAGATAGAGCTCAGGGTGCTGGCCCAC-CTCTCCGGCGACGAGAACCTGATCCG GGTCTTC-CAGGAGGGGCGGGACATCCACACG-GAGACCGCCAGCTGGATGTTCGG CGTCCCCCGGGAGGCCGTGGACCCCCT-GATGCGCCGGGCGGCCAAGACCATCAA CTTCGGGGTCCTCTACGGCATGTCGGC-CCACCGCCTCTCCCAGGAGCTAGCCATC CCTTAC-GAGGAGGCCCAGGCCTTCATTGAGCGC-TACTTTCAGAGCTTCCCCAAGG TGCGGGCCTGGATTGAGAAGACCCTG-GAGGAGGGCAGGAGGCGGGGGTACGTG GAGAC-CCTCTTCGGCCGCCGCCGCTACGTGCCA-GACCTAGAGGCCCGGGTGAAG AGCGTGCGGGAGGCGGCCGAGCGCATG-GCCTTCAACATGCCCGTCCAGGGCACC GCCGC-CGACCTCATGAAGCTGGCTATGGT-GAAGCTCTTCCCCAGGCTGGAGGAA ATGGGGGCCAGGATGCTCCTTCAGGTC-CACGACGAGCTGGTCCTCGAGGCCCCA AAA-GAGAGGGCGGAGGCCGTGGCCCGGCTG-GCCAAGGAGGTCATGGAGGGGGT GTATCCCCTGGCCGTGCCCCTGGAGGTG-GAGGTGGGGATAGGGGAGGACTGGCT CTCCGC-CAAGGAGGGCATTGATGGCCGCGGCG-GAGGCGGGCATCATCATCATCA TCATTAA

SEQ ID NO:10 The amino acid sequence of the Sac7d-ΔTaq fusion protein

MITNSTVKVKFKYK-GEEKEVDTSKIKKVWRVGKMVSFTYDD-NGKTGRGAVSEKDA PKELLDM-LARAEREKKGGGVTSPKALEEAPWPPPEGAFV-GFVLSRKEPMWADLLAL AAARGGRVHRAPEP-YKALRDLKEARGLLAKDLSVLAL-REGLGLPPGDDPMLLAYLL DPSNTTPEG-VARRYGGEWTEEAGERAALSERLFANLWGRLE-GEERLLWLYREVERP LSAVLAHMEATGVRLDVAY-LRALSLEVAEEIARLEAEVFRLAGH-PFNLNSRDQLERV LFDELGLPAIGKTEKTGKRST-SAAVLEALREAHPIVEKILQYRELTKLKSTYID-PLPDLI HPRTGRLHTRFNQTATATGRLSSSDPN-LQNIPVRTPLGQRIRRAFIAEEGWLLVALDY SQIEL-RVLAHLSGDENLIRVFQEGRDIHTETA-SWMFGVPREAVDPLMRRAAKTINFG VLYGMSAHRLSQELAIPYEEAQAFIERY-FQSFPKVRAWIEKTLEEGRRRGYVETLFGR RRYVPDLEARVKSVREAAERMAFN-MPVQGTAADLMKLAMVKLFPRLEEMGARML

LQVHDELVLEAPKERAEAVAR-LAKEVMEGVYPLAVPLEVEVGIGEDWL-SAKEGIDG RGGGGHHHHHH

SEQ ID NO:11 The DNA sequence encoding the PL-ΔTaq fusion protein

ATGATTACGAATTCGAAGAAAAA-GAAAAAGAAAAAGCGTAAGAAACGCAAAAA GAAAAAGAAAGGCGGCGGTGTCAC-TAGTGGCGCAACCGTAAAGTTCAAGTACAA AGGCGAAGAAAAAGAGGTAGACATCTC-CAAGATCAAGAAAGTATGGCGTGTGG GCAAGAT-GATCTCCTTCACCTACGACGAGGGCG-GTGGCAAGACCGGCCGTGGTG CGGTAAGCGAAAAGGACGCGCCGAAG-GAGCTGCTGCAGATGCTGGAGAAGCAG AAAAAGGGCGGCGGTGTCACCAGTC-CCAAGGCCCTGGAGGAGGCCCCCTGGCCC CCGCCGGAAGGGGCCT-TCGTGGGCTTTGTGCTTTCCCGCAAG-GAGCCCATGTGGG CCGATCTTCTGGCCCTGGC-CGCCGCCAGGGGGGGCCGGGTCCACCGGGCC-CCCG AGCCTTATAAAGCCCTCAGGGACCT-GAAGGAGGCGCGGGGGCTTCTCGCCAAAG ACCTGAGCGTTCTGGCCCTGAGGGAAG-GCCTTGGCCTCCCGCCCGGCGACGACCC CAT-GCTCCTCGCCTACCTCCTGGACCCTTC-CAACACCACCCCCGAGGGGGTGGCC CGGCGCTACGGCGGGGAGTGGACGGAG-GAGGCGGGGGAGCGGGCCGCCCTTTCC GAGAG-GCTCTTCGCCAACCTGTGGGGGAGGCT-TGAGGGGGAGGAGAGGCTCCTT TGGCTTTACCGGGAGGTGGAGAGGC-CCCTTTCCGCTGTCCTGGCCCACATGGAGG CCACGGGGGTGCGCCTGGACGTGGC-CTATCTCAGGGCCTTGTCCCTGGAGGTGGC CGAGGAGATCGCCCGCCTCGAGGCCGAG-GTCTTCCGCCTGGCCGGCCACCCCTTC AACCT-CAACTCCCGGGACCAGCTGGAAAGGGTC-CTCTTTGACGAGCTAGGGCTTC CCGCCATCGGCAAGACGGAGAAGACCG-GCAAGCGCTCCACCAGCGCCGCCGTCC TGGAG-GCCCTCCGCGAGGCCCACCCCATCGTG-GAGAAGATCCTGCAGTACCGGG AGCTCACCAAGCTGAAGAGCACCTACAT-TGACCCCTTGCCGGACCTCATCCACCC CAG-GACGGGCCGCCTCCACACCCGCTTCAAC-CAGACGGCCACGGCCACGGGCAG GCTAAGTAGCTCCGATCCCAACCTCCA-GAACATCCCCGTCCGCACCCCGCTTGGG CAGAG-GATCCGCCGGGCCTTCATCGCCGAG-GAGGGGTGGCTATTGGTGGCCCTG GACTATAGCCAGATAGAGCTCAGGGT-GCTGGCCCACCTCTCCGGCGACGAGAAC CTGATCCGGGTCTTCCAGGAGGGGCGG-GACATCCACACGGAGACCGCCAGCTGG ATGT-TCGGCGTCCCCCGGGAGGCCGTGGAC-CCCCTGATGCGCCGGGCGGCCAAG ACCATCAACTTCGGGGTCCTCTACG-GCATGTCGGCCCACCGCCTCTCCCAGGAGC TAGCCATCCCTTACGAGGAGGCCCAGGC-CTTCATTGAGCGCTACTTTCAGAGCTT CCCCAAG-GTGCGGGCCTGGATTGAGAAGACCCTG-GAGGAGGGCAGGAGGCGGG GGTACGTGGAGACCCTCTTCGGCCGC-CGCCGCTACGTGCCAGACCTAGAGGCCC GGGT-GAAGAGCGTGCGGGAGGCGGCCGAGCG-CATGGCCTTCAACATGCCCGTCC AGGGCACCGCCGCCGACCTCAT-GAAGCTGGCTATGGTGAAGCTCTTCCCCAGGCT GGAGGAAATGGGGGCCAGGATGCTCCT-TCAGGTCCACGACGAGCTGGTCCTCGA GGC-CCCAAAAGAGAGGGCGGAGGCCGTGGC-CCGGCTGGCCAAGGAGGTCATGG AGGGGGTGTATCCCCTGGCCGTGC-CCCTGGAGGTGGAGGTGGGGATAGGGGAGG ACTGGCTCTCCGCCAAGGAGGGCAT-TGATGGCCGCGGCGGAGGCGGGCATCATC ATCATCATCATTAA

SEQ ID NO:12 The amino acid sequence of PL-ΔTaq fusion protein

MITNSKKKKKKKRKKRKKKKKGGGVTS-GATVKFKYKGEEKEVDISKIKKVWRVGK MISFTY-DEGGGKTGRGAVSEKDAPKELLQMLE-KQKKGGGVTSPKALEEAPWPPPEG AFVGFVLSRKEPMWADLLALAAARG-GRVHRAPEPYKALRDLKEARGLLAKDLSVL ALREGLGLPPGDDPMLLAYLLDPSNT-TPEGVARRYGGEWTEEAGERAALSERLFAN LWGRLEGEERLLWLYREVERPLSAVLAH-MEATGVRLDVAYLRALSLEVAEEIARLE AEVFR-LAGHPFNLNSRDQLERVLFDEL-GLPAIGKTEKTGKRSTSAAVLEALREAHPIV EKILQYRELTKLKSTYIDPLPDLIHPRT-GRLHTRFNQTATATGRLSS SDPNLQNIPVRTP LGQRIRRAFIAEEGWLLVALDYSQIEL-RVLAHLSGDENLIRVFQEGRDIHTETASWMF GVPREAVDPLMRRAAKTINFGVLYGM-SAHRLSQELAIPYEEAQAFIERYFQSFPKVRAWIEK-TLEEGRRRGYVETLFGRRRYVPDLE-ARVKSVREAAERMAFNMPVQGTAAD LMKLAMVKLFPRLEEMGARMLLQVH-DELVLEAPKERAEAVARLAKEVMEGVYPL AVPLEVEVGIGEDWLSAKEGIDGRGGGGHHHHHH

SEQ ID NO:13 PRIMER L71F
5'-CCTGCTCTGCCGCTTCACGC-3'

SEQ ID NO:14 PRIMER L71R
5'-GCACAGCGGCTGGCTGAGGA-3'

SEQ ID NO:15 PRIMER L18015F
5'-TGACGGAGGATAACGCCAGCAG-3'

SEQ ID NO:16 PRIMER L23474R
5'-GAAAGACGA TGGGTCGCTAATACGC-3'

SEQ ID NO:17 PRIMER L18015F
5'-TGACGGAGGATAAC GCCAGCAG-3'

SEQ ID NO:18 PRIMER L29930R
5'-GGGGTTGGAGGTCAATGGGTTC-3 '

SEQ ID NO:19 PRIMER L30350F
5'-CCTGCTCTGCCGCTTCACGC-3'

SEQ ID NO:20 PRIMER L35121R
5'-CACATGGTACAGCAAGCCTGGC-3'

SEQ ID NO:21 PRIMER L2089F p0 5'-CCCGTATCT-GCTGGGA TACTGGC-3

SEQ ID NO:22 PRIMER L7112R
5'-CAGCGGTGCTGACTGAATCATGG-3

SEQ ID NO:23 PRIMER L30350F
5'-CCTGCCTGCCGCTTCACGC-3'

SEQ ID NO:24 PRIMER L40547R
5'-CCAATACCCGTTTCA TCGCGGC-3'

SEQ ID NO:25 PRIMER H-Amelo-Y
5'-CCACCTCATCCTGG GCACC-3'

SEQ ID NO:26 PRIMER H-Amelo-YR
5'-GCTTGAGGCCAACCATCAGAGC-3'

SEQ ID NO:27 Human beta-globin primer 536F
5'-GGTTGGCCAATCTACTCCCAGG-3'

SEQ ID NO:28 Human beta-globin primer 536R
5'-GCTCACTCAGTGTGGCAAAG-3'

SEQ ID NO:29 Human beta-globin primer 1408R
5'-GATTAGCAAAAGGGCCTAGCTTGG-3'

What is claimed is:

1. A protein comprising two joined heterologous domains:

a sequence non-specific double-stranded nucleic acid binding domain that comprises an amino acid sequence that has at least 75% sequence identity to SEQ ID NO:2; and a DNA polymerase domain wherein the presence of the sequence non-specific double-stranded nucleic acid binding domain enhances the processivity of the polymerase domain compared to an identical protein that does not have the sequence non-specific double-stranded nucleic acid binding domain joined thereto.

2. The protein of claim 1, wherein the sequence non-specific double-stranded nucleic acid binding domain and the DNA polymerase domain are covalently linked.

3. The protein of claim 1, wherein the DNA polymerase domain has thermally stable polymerase activity.

4. The protein of claim 1, wherein the DNA polymerase domain comprises a family A polymerase domain.

5. The protein of claim 4, wherein the family A polymerase domain is a *Thermus* polymerase domain.

6. The protein of claim 4, wherein the family A polymerase domain is a Taq polymerase domain.

7. The protein of claim 3, wherein the DNA polymerase domain is a ΔTaq domain.

8. The protein of claim 1, wherein the polymerase domain is a family B polymerase domain.

9. The protein of claim 8, wherein the family B polymerase domain is a *Pyrococcus* DNA polymerase I domain.

10. The protein of claim 9, wherein the *Pyrococcus* polymerase domain is a *Pyrococcus furiosus* domain.

11. A protein comprising two joined heterologous domains:

a sequence non-specific double-stranded nucleic acid binding domain that comprises an amino acid sequence that has at least 75% sequence identity to the Sac7d sequence set forth in amino acids 7-71 of SEQ ID NO:10; and a DNA polymerase domain, wherein the presence of the sequence non-specific double-stranded nucleic acid binding domain enhances the processivity of the polymerase domain compared to an identical protein that does not have the sequence non-specific double-stranded nucleic acid binding domain joined thereto.

12. The protein of claim 11, wherein the sequence non-specific double-stranded nucleic acid binding domain and the DNA polymerase domain are covalently linked.

13. The protein of claim 11, wherein the sequence non-specific double-stranded nucleic acid binding domain comprises an amino acid sequence that has at least 90% sequence identity to the Sac 7d sequence set forth in SEQ ID NO:10.

14. The protein of claim 11, wherein the DNA polymerase domain has thermally stable polymerase activity.

15. The protein of claim 11, wherein the DNA polymerase domain comprises a family A polymerase domain.

16. The protein of claim 14, wherein the DNA polymerase domain is a *Thermus* polymerase domain.

17. The protein of claim 16, wherein the *Thermus*polymerase domain is a Taq polymerase domain.

18. The protein of claim 14, wherein the DNA polymerase domain is a ΔTaq domain.

19. The protein of claim 11, wherein the polymerase domain is a family B polymerase domain.

20. The protein of claim 19, wherein the family B polymerase domain is a *Pyrococcus* DNA polymerase I domain.

21. The protein of claim 20, wherein the *Pyrococcus* polymerase domain is a *Pyrococcus furiosus* domain.

22. The protein of claim 1, wherein the sequence non-specific double-stranded nucleic acid binding domain comprises an amino acid sequence that has at least 85% sequence identity to SEQ ID NO:2.

23. The protein of claim 11, wherein the sequence non-specific double-stranded nucleic acid binding domain comprises an amino acid sequence that has at least 85% sequence identity to the Sac 7d sequence set forth in SEQ ID NO:10.

* * * * *